United States Patent [19]

Bannwarth et al.

[11] Patent Number: 5,702,918
[45] Date of Patent: Dec. 30, 1997

[54] HIV-2 ENVELOPE POLYPEPTIDES

[75] Inventors: Wilhelm Bannwarth, Rheinfelden-Beuggen, Germany; Patrick Caspers, Oberwil, Switzerland; Stuart Le Grice, Basel, Switzerland; Jan Mous, Giebenach, Switzerland

[73] Assignee: Roche Diagnostic Systems, Inc., Branchburg, N.J.

[21] Appl. No.: 435,937

[22] Filed: May 5, 1995

Related U.S. Application Data

[63] Continuation of Ser. No. 213,416, Mar. 15, 1994, which is a continuation of Ser. No. 895,977, Jun. 9, 1992, abandoned, which is a continuation of Ser. No. 268,322, Nov. 7, 1988, abandoned.

[30] Foreign Application Priority Data

Nov. 16, 1987 [CH] Switzerland .............. 4454/87

[51] Int. Cl.$^6$ .............. C12P 21/06; C12Q 1/70; C07K 1/00; C07K 14/00
[52] U.S. Cl. .............. 435/69.3; 435/5; 435/7.1; 435/69.1; 530/395; 530/350; 530/416
[58] Field of Search .............. 435/5, 7.1, 69.1, 435/69.3; 530/495, 350, 416

[56] References Cited

U.S. PATENT DOCUMENTS

| | | | |
|---|---|---|---|
| 4,569,794 | 2/1986 | Smith et al. | 260/113 |
| 4,812,556 | 3/1989 | Vahine et al. | 530/324 |
| 4,925,784 | 5/1990 | Crowl et al. | 435/5 |

FOREIGN PATENT DOCUMENTS

| | | |
|---|---|---|
| 0284383 | 9/1988 | European Pat. Off. |
| 0339389 | 11/1989 | European Pat. Off. |
| 874860 | 7/1987 | South Africa |
| 880310 | 1/1988 | South Africa |
| WO 84/03564 | 3/1984 | WIPO |
| WO 87/04459 | 7/1987 | WIPO |
| WO 88/05440 | 7/1988 | WIPO |

OTHER PUBLICATIONS

Translation of EPA 0 339,389.
Pongor, 1987, "Use of Structural Profiles and ...". Methods in Enzymology 154: 450–473.

Clavel, et al., 1986, "Molecular Cloning and Polymorphism ..." Nature 324:691–695.

Clavel, et al., 1986, "Isolation of a New Human ..." Science 233: 343–346.

Kyte and Doolittle, J. Mol. Biol. 157:105–132 (1982) "A Simple Method for Displaying the Hydropathic Character of a Protein".

Pauletti, et al., Anal. Biochem. 151:540–546 (1985) "Application of a Modified Computer Algorithm in Determining Potential Antigenic Determinants Asso. with the ...".

Hopp and Woods, Proc. Natl. Acid. Sci. 78(6):3824–3828 (1981) "Prediction of Protein Antigenic Determinants from Amino Acid Sequences".

Cordonnier, et al., Nature 340:571–574 (1989) "Single Amino Acid Changes in HIV ...".

Guyader, et al., Nature 326:662–669 (1987) "Genome Organization and Transactivation of the Human Immunodeficiency Virus Type 2".

Hochuli, et al., Biol. Chem. Hoppe–Seyler 368:748 (1987) "Alpha–alkyl Nitrilotriacetic Acid Adsorbants ...".

Villarejo, et al., J. Bacteriol. 120:466–474 (1974) "Beta Galactosidase from Termination and Deletion Mutant Strains".

Certa, et al., EMBO J.5(11):3051–3056 (1986) "Subregions of a Conserved Part of the HIV ...".

Shoeman, et al., Anal. Biochem. 161:370–379 (1987) "Comparison of Recombinant Human Immunodeficiency ...".

*Primary Examiner*—Lynette F. Smith
*Attorney, Agent, or Firm*—George W. Johnston; Patricia S. Rocha-Tramaloni

[57] ABSTRACT

Polypeptides which include at least one antigenic and/or immunogenic determinant of the envelope protein (env) of the HIV-2 virus and their production by recombinant DNA technology and the DNA sequences, expression vectors and transformed single-cell organisms used in this process are provided. A method for the detection of HIV antibodies or HIV viruses in human sera or in other biological fluids is also provided.

5 Claims, 29 Drawing Sheets

SerAlaArgLeuAsnSerTrpGlyCysAlaPheArgArgGlnValCysHisThrThrThrValProTrpValAsnAspSerLeuAlaProAsp
GATCCGCTCGTCTGAACTCCTGGGGTTGCGCTTTTCGCGTTGCCACACTACGGTGGGTAAACGACAGTTAGCTCCGGAC
GCGAGCAGACTTGAGGACCCCAACGCGAAAAGCAGTCCAAACGGTGTGATGCCATGGCACCCATTGCTGTCGAGGCCTG

TrpAspAsnMetThrTrpGlnGluTrpGluLysGlnValAlaArgTyrLeuGluAlaAsnIleSerLysSerLeuGluGlnAlaGlnGly
TGGGATAACATGACTTGGCAGGAATGGGAAAAACAGGTGCGCTAACATTCTAAATCTCTGAACAGGCTCAGG
ACCCTATTGTACTGAACCGTCCTTACCCTTTTTGTCCACGCGATGACCTCCGATTGTAAGATTTAGAGACCTTGTCCGAGTCCCTAG

FIG. 1

N250PSN250P29

```
        10         20         30         40         50
        |          |          |          |          |
   1 CTCGAGAAAT CATAAAAAAT TTATTTGCTT TGTGAGCGGA TAACAATTAT
  51 AATAGATTCA ATTGTGAGCG GATAACAATT TCACACAGAA TTCATTAAAG
 101 AGGAGAAATT AACTATGAGA GGATCCGGCA TCATGGTTCG ACCATTGAAC
 151 TGCATCGTCG CCGTGTCCCA AAATATGGGG ATTGGCAAGA ACGGAGACCT
 201 ACCCTGGCCT CCGCTCAGGA ACGAGTTCAA GTACTTCCAA AGAATGACCA
 251 CAACCTCTTC AGTGGAAGGT AAACAGAATC TGGTGATTAT GGGTAGGAAA
 301 ACCTGGTTCT CCATTCCTGA GAAGAATCGA CCTTTAAAGG ACAGAATTAA
 351 TATAGTTCTC AGTAGAGAAC TCAAAGAACC ACCACGAGGA GCTCATTTTC
 401 TTGCCAAAAG TTTGGATGAT GCCTTAAGAC TTATTGAACA ACCGGAATTG
 451 GCAAGTAAAG TAGACATGGT TTGGATAGTC GGAGGCAGTT CTGTTTACCA
 501 GGAAGCCATG AATCAACCAG GCCACCTTAG ACTCTTTGTG ACAAGGATCA
 551 TGCAGGAATT TGAAAGTGAC ACGTTTTTCC CAGAAATTGA TTTGGGGAAA
 601 TATAAACTTC TCCCAGAATA CCCAGGCGTC CTCTCTGAGG TCCAGGAGGA
 651 AAAAGGCATC AAGTATAAGT TTGAAGTCTA CGAGAAGAAA GGTTCCAGAT
 701 CTGTTAACCT AGTTTAACAG GAAGATGCTT TCAAGTTCTC TGCTCCCCTC
 751 CTAAAGCTAT GCATTTTTAT AAGACCATGG GACTTTGCT GGCTTTAGAT
 801 CCGGCCAAGC TTGGACTCCT GTTGATAGAT CCAGTAATGA CCTCAGAACT
 851 CCATCTGGAT TTGTTCAGAA CGCTCGGTTG CCGCCGGGCG TTTTTTATTG
 901 GTGAGAATCC AAGCTAGCTT GGCGAGATTT TCAGGAGCTA AGGAAGCTAA
 951 AATGGAGAAA AAAATCACTG GATATACCAC CGTTGATATA TCCCAATGGC
1001 ATCGTAAAGA ACATTTTGAG GCATTTCAGT CAGTTGCTCA ATGTACCTAT
1051 AACCAGACCG TTCAGCTGGA TATTACGGCC TTTTTAAAGA CCGTAAAGAA
1101 AAATAAGCAC AAGTTTTATC CGGCCTTTAT TCACATTCTT GCCCGCCTGA
1151 TGAATGCTCA TCCGGAATTT CGTATGGCAA TGAAAGACGG TGAGCTGGTG
```

*FIG. 3A*

1201 ATATGGGATA GTGTTCACCC TTGTTACACC GTTTTCCATG AGCAAACTGA

1251 AACGTTTTCA TCGCTCTGGA GTGAATACCA CGACGATTTC CGGCAGTTTC

1301 TACACATATA TTCGCAAGAT GTGGCGTGTT ACGGTGAAAA CCTGGCCTAT

1351 TTCCCTAAAG GGTTTATTGA GAATATGTTT TTCGTCTCAG CCAATCCCTG

1401 GGTGAGTTTC ACCAGTTTTG ATTTAAACGT GGCCAATATG GACAACTTCT

1451 TCGCCCCCGT TTTCACCATG GGCAAATATT ATACGCAAGG CGACAAGGTG

1501 CTGATGCCGC TGGCGATTCA GGTTCATCAT GCCGTCTGTG ATGGCTTCCA

1551 TGTCGGCAGA ATGCTTAATG AATTACAACA GTACTGCGAT GAGTGGCAGG

1601 GCGGGGCGTA ATTTTTTTAA GGCAGTTATT GGTGCCCTTA AACGCCTGGG

1651 GTAATGACTC TCTAGCTTGA GGCATCAAAT AAAACGAAAG GCTCAGTCGA

1701 AAGACTGGGC CTTTCGTTTT ATCTGTTGTT TGTCGGTGAA CGCTCTCCTG

1751 AGTAGGACAA ATCCGCCGCT CTAGAGCTGC CTCGCGCGTT TCGGTGATGA

1801 CGGTGAAAAC CTCTGACACA TGCAGCTCCC GGAGACGGTC ACAGCTTGTC

1851 TGTAAGCGGA TGCCGGGAGC AGACAAGCCC GTCAGGGCGC GTCAGCGGGT

1901 GTTGGCGGGT GTCGGGCGC AGCCATGACC CAGTCACGTA GCGATAGCGG

1951 AGTGTATACT GGCTTAACTA TGCGGCATCA GAGCAGATTG TACTGAGAGT

2001 GCACCATATG CGGTGTGAAA TACCGCACAG ATGCGTAAGG AGAAAATACC

2051 GCATCAGGCG CTCTTCCGCT TCCTCGCTCA CTGACTCGCT GCGCTCGGTC

2101 TGTCGGCTGC GGCGAGCGGT ATCAGCTCAC TCAAAGGCGG TAATACGGTT

2151 ATCCACAGAA TCAGGGGATA ACGCAGGAAA GAACATGTGA GCAAAAGGCC

2201 AGCAAAAGGC CAGGAACCGT AAAAAGGCCG CGTTGCTGGC GTTTTTCCAT

2251 AGGCTCCGCC CCCCTGACGA GCATCACAAA AATCGACGCT CAAGTCAGAG

2301 GTGGCGAAAC CCGACAGGAC TATAAAGATA CCAGGCGTTT CCCCCTGGAA

2351 GCTCCCTCGT GCGCTCTCCT GTTCCGACCC TGCCGCTTAC CGGATACCTG

2401 TCCGCCTTTC TCCCTTCGGG AAGCGTGGCG CTTTCTCAAT GCTCACGCTG

2451 TAGGTATCTC AGTTCGGTGT AGGTCGTTCG CTCCAAGCTG GGCTGTGTGC

2501 ACGAACCCCC CGTTCAGCCC GACCGCTGCG CCTTATCCGG TAACTATCGT

*FIG. 3B*

2551 CTTGAGTCCA ACCCGGTAAG ACACGACTTA TCGCCACTGG CAGCAGCCAC

2601 TGGTAACAGG ATTAGCAGAG CGAGGTATGT AGGCGGTGCT ACAGAGTTCT

2651 TGAAGTGGTG GCCTAACTAC GGCTACACTA GAAGGACAGT ATTTGGTATC

2701 TGCGCTCTGC TGAAGCCAGT TACCTTCGGA AAAAGAGTTG GTAGCTCTTG

2751 ATCCGGCAAA CAAACCACCG CTGGTAGCGG TGGTTTTTTT GTTTGCAAGC

2801 AGCAGATTAC GCGCAGAAAA AAAGGATCTC AAGAAGATCC TTTGATCTTT

2851 TCTACGGGGT CTGACGCTCA GTGGAACGAA AACTCACGTT AAGGGATTTT

2901 GGTCATGAGA TTATCAAAAA GGATCTTCAC CTAGATCCTT TTAAATTAAA

2951 AATGAAGTTT TAAATCAATC TAAAGTATAT ATGAGTAAAC TTGGTCTGAC

3001 AGTTACCAAT GCTTAATCAG TGAGGCACCT ATCTCAGCGA TCTGTCTATT

3051 TCGTTCATCC ATAGCTGCCT GACTCCCCGT CGTGTAGATA ACTACGATAC

3101 GGGAGGGCTT ACCATCTGGC CCCAGTGCTG CAATGATACC GCGAGACCCA

3151 CGCTCACCGG CTCCAGATTT ATCAGCAATA AACCAGCCAG CCGGAAGGGC

3201 CGAGCGCAGA AGTGGTCCTG CAACTTTATC CGCCTCCATC CAGTCTATTA

3251 ATTGTTGCCG GGAAGCTAGA GTAAGTAGTT CGCCAGTTAA TAGTTTGCGC

3301 AACGTTGTTG CCATTGCTAC AGGCATCGTG GTGTCACGCT CGTCGTTTGG

3351 TATGGCTTCA TTCAGCTCCG GTTCCCAACG ATCAAGGCGA GTTACATGAT

3401 CCCCCATGTT GTGCAAAAAA GCGGTTAGCT CCTTCGGTCC TCCGATCGTT

3451 GTCAGAAGTA AGTTGGCCGC AGTGTTATCA CTCATGGTTA TGGCAGCACT

3501 GCATAATTCT CTTACTGTCA TGCCATCCGT AAGATGCTTT TCTGTGACTG

3551 GTGAGTACTC AACCAAGTCA TTCTGAGAAT AGTGTATGCG GCGACCGAGT

3601 TGCTCTTGCC CGGCGTCAAT ACGGGATAAT ACCGCGCCAC ATAGCAGAAC

3651 TTTAAAAGTG CTCATCATTG GAAAACGTTC TTCGGGGCGA AAACTCTCAA

3701 GGATCTTACC GCTGTTGAGA TCCAGTTCGA TGTAACCCAC TCGTGCACCC

3751 AACTGATCTT CAGCATCTTT TACTTTCACC AGCGTTTCTG GGTGAGCAAA

3801 AACAGGAAGG CAAAATGCCG CAAAAAAGGG AATAAGGGCG ACACGGAAAT

3851 GTTGAATACT CATACTCTTC CTTTTTCAAT ATTATTGAAG CATTTATCAG

3901 GGTTATTGTC TCATGAGCGG ATACATATTT GAATGTATTT AGAAAAATAA

*FIG. 3C*

```
3951 ACAAATAGGG GTTCCGCGCA CATTTCCCCG AAAAGTGCCA CCTGACGTCT

4001 AAGAAACCAT TATTATCATG ACATTAACCT ATAAAAATAG GCGTATCACG

4051 AGGCCCTTTC GTCTTCAC
```

*FIG. 3D*

|     | 10         | 20         | 30         | 40         | 50         |
|-----|------------|------------|------------|------------|------------|
| 1   | AAGCTTCACG | CTGCCGCAAG | CACTCAGGGC | GCAAGGGCTG | CTAAAGGAAG |
| 51  | CGGAACACGT | AGAAAGCCAG | TCCGCAGAAA | CGGTGCTGAC | CCCGGATGAA |
| 101 | TGTCAGCTAC | TGGGCTATCT | GGACAAGGGA | AAACGCAAGC | GCAAAGAGAA |
| 151 | AGCAGGTAGC | TTGCAGTGGG | CTTACATGGC | GATAGCTAGA | CTGGGCGGTT |
| 201 | TTATGGACAG | CAAGCGAACC | GGAATTGCCA | GCTGGGGCGC | CCTCTGGTAA |
| 251 | GGTTGGGAAG | CCCTGCAAAG | TAAACTGGAT | GGCTTTCTTG | CCGCCAAGGA |
| 301 | TCTGATGGCG | CAGGGGATCA | AGATCTGATC | AAGAGACAGG | ATGAGGATCG |
| 351 | TTTCGCATGA | TTGAACAAGA | TGGATTGCAC | GCAGGTTCTC | CGGCCGCTTG |
| 401 | GGTGGAGAGG | CTATTCGGCT | ATGACTGGGC | ACAACAGACA | ATCGGCTGCT |
| 451 | CTGATGCCGC | CGTGTTCCGG | CTGTCAGCGC | AGGGGCGCCC | GGTTCTTTTT |
| 501 | GTCAAGACCG | ACCTGTCCGG | TGCCCTGAAT | GAACTGCAGG | ACGAGGCAGC |
| 551 | GCGGCTATCG | TGGCTGGCCA | CGACGGGCGT | TCCTTGCGCA | GCTGTGCTCG |
| 601 | ACGTTGTCAC | TGAAGCGGGA | AGGGACTGGC | TGCTATTGGG | CGAAGTGCCG |
| 651 | GGGCAGGATC | TCCTGTCATC | TCACCTTGCT | CCTGCCGAGA | AAGTATCCAT |
| 701 | CATGGCTGAT | GCAATGCGGC | GGCTGCATAC | GCTTGATCCG | GCTACCTGCC |
| 751 | CATTCGACCA | CCAAGCGAAA | CATCGCATCG | AGCGAGCACG | TACTCGGATG |
| 801 | GAAGCCGGTC | TTGTCGATCA | GGATGATCTG | GACGAAGAGC | ATCAGGGGCT |
| 851 | CGCGCCAGCC | GAACTGTTCG | CCAGGCTCAA | GGCGCGCATG | CCCGACGGCG |
| 901 | AGGATCTCGT | CGTGACCCAT | GGCGATGCCT | GCTTGCCGAA | TATCATGGTG |
| 951 | GAAAATGGCC | GCTTTTCTGG | ATTCATCGAC | TGTGGCCGGC | TGGGTGTGGC |
| 1001| GGACCGCTAT | CAGGACATAG | CGTTGGCTAC | CCGTGATATT | GCTGAAGAGC |
| 1051| TTGGCGGCGA | ATGGGCTGAC | CGCTTCCTCG | TGCTTTACGG | TATCGCCGCT |
| 1101| CCCGATTCGC | AGCGCATCGC | CTTCTATCGC | CTTCTTGACG | AGTTCTTCTG |
| 1151| AGCGGGACTC | TGGGGTTCGA | AATGACCGAC | CAAGCGACGC | CCAACCTGCC |

FIG. 6A

1201 ATCACGAGAT TTCGATTCCA CCGCCGCCTT CTATGAAAGG TTGGGCTTCG

1251 GAATCGTTTT CCGGGACGCC GGCTGGATGA TCCTCCAGCG CGGGGATCTC

1301 ATGCTGGAGT TCTTCGCCCA CCCCGGGCTC GATCCCCTCG CGAGTTGGTT

1351 CAGCTGCTGC CTGAGGCTGG ACGACCTCGC GGAGTTCTAC CGGCAGTGCA

1401 AATCCGTCGG CATCCAGGAA ACCAGCAGCG GCTATCCGCG CATCCATGCC

1451 CCCGAACTGC AGGAGTGGGG AGGCACGATG GCCGCTTTGG TCGACAATTC

1501 GCGCTAACTT ACATTAATTG CGTTGCGCTC ACTGCCCGCT TTCCAGTCGG

1551 GAAACCTGTC GTGCCAGCTG CATTAATGAA CTGGCCAACG CGCGGGGAGA

1601 GGCGGTTTGC GTATTGGGCG CCAGGGTGGT TTTTCTTTTC ACCAGTGAGA

1651 CGGGCAACAG CTGATTGCCC TTCACCGCCT GGCCCTGAGA GAGTTGCAGC

1701 AAGCGGTCCA CGCTGGTTTG CCCCAGCAGG CGAAAATCCT GTTTGATGGT

1751 GGTTAACGGC GGGATATAAC ATGAGCTGTC TTCGGTATCG TCGTATCCCA

1801 CTACCGAGAT ATCCGCACCA ACGCGCAGCC CGGACTCGGT AATGGCGCGC

1851 ATTGCGCCCA GCGCCATCTG ATCGTTGGCA ACCAGCATCG CAGTGGGAAC

1901 GATGCCCTCA TTCAGCATTT GCATGGTTTG TTGAAAACCG GACATGGCAC

1951 TCCAGTCGCC TTCCCGTTCC GCTATCGGCT GAATTTGATT GCGAGTGAGA

2001 TATTTATGCC AGCCAGCCAG ACGCAGACGC GCCGAGACAG AACTTAATGG

2051 GCCCGCTAAC AGCGCGATTT GCTGGTGACC CAATGCGACC AGATGCTCCA

2101 CGCCCAGTCG CGTACCGTCT TCATGGGAGA AAATAATACT GTTGATGGGT

2151 GTCTGGTCAG AGACATCAAG AAATAACGCC GGAACATTAG TGCAGGCAGC

2201 TTCCACAGCA ATGGCATCCT GGTCATCCAG CGGATAGTTA ATGATCAGCC

2251 CACTGACGCG TTGCGCGAGA AGATTGTGCA CCGCCGCTTT ACAGGCTTCG

2301 ACGCCGCTTC GTTCTACCAT CGACACCACC ACGCTGGCAC CCAGTTGATC

2351 GGCGCGAGAT TTAATCGCCG CGACAATTTG CGACGGCGCG TGCAGGGCCA

2401 GACTGGAGGT GGCAACGCCA ATCAGCAACG ACTGTTTGCC CGCCAGTTGT

2451 TGTGCCACGC GGTTGGGAAT GTAATTCAGC TCCGCCATCG CCGCTTCCAC

2501 TTTTTCCCGC GTTTTCGCAG AAACGTGGCT GGCCTGGTTC ACCACGCGGG

2551 AAACGGTCTG ATAAGAGACA CCGGCATACT CTGCGACATC GTATAACGTT

FIG. 5B

2601 ACTGGTTTCA CATTCACCAC CCTGAATTGA CTCTCTTCCG GGCGCTATCA

2651 TGCCATACCG CGAAAGGTTT TGCACCATTC GATGGTGTCA ACGTAAATGC

2701 ATGCCGCTTC GCCTTCGCGC GCGAATTGTC GACCCTGTCC CTCCTGTTCA

2751 GCTACTGACG GGGTGGTGCG TAACGGCAAA AGCACCGCCG GACATCAGCG

2801 CTAGCGGAGT GTATACTGGC TTACTATGTT GGCACTGATG AGGGTGTCAG

2851 TGAAGTGCTT CATGTGGCAG GAGAAAAAG GCTGCACCGG TGCGTCAGCA

2901 GAATATGTGA TACAGGATAT ATTCCGCTTC CTCGCTCACT GACTCGCTAC

2951 GCTCGGTCGT TCGACTGCGG CGAGCGGAAA TGGCTTACGA ACGGGCGGA

3001 GATTTCCTGG AAGATGCCAG GAAGATACTT AACAGGGAAG TGAGAGGGCC

3051 GCGGCAAAGC CGTTTTTCCA TAGGCTCCGC CCCCTGACA AGCATCACGA

3151 ACCAGGCGTT TCCCCTGGCG GCTCCCTCGT GCGCTCTCCT GTTCCTGCCT

3201 TTCGGTTTAC CGGTGTCATT CCGCTGTTAT GGCCGCGTTT GTCTCATTCC

3251 ACGCCTGACA CTCAGTTCCG GGTAGGCAGT TCGCTCCAAG CTGGACTGTA

3301 TGCACGAACC CCCCGTTCAG TCCGACCGCT GCGCCTTATC CGGTAACTAT

3351 CGTCTTGAGT CCAACCCGGA AAGACATGCA AAAGCACCAC TGGCAGCAGC

3401 CACTGGTAAT TGATTTAGAG GAGTTAGTCT TGAAGTCATG CGCCGGTTAA

3451 GGCTAAACTG AAAGGACAAG TTTTGGTGAC TGCGCTCCTC CAAGCCAGTT

3501 ACCTCGGTTC AAAGAGTTGG TAGCTCAGAG AACCTTCGAA AAACCGCCCT

3551 GCAAGGCGGT TTTTTCGTTT TCAGAGCAAG AGATTACGCG CAGACCAAAA

3601 CGATCTCAAG AAGATCATCT TATTAATCAG ATAAAATATT TCTAGATTTC

3651 AGTGCAATTT ATCTCTTCAA ATGTAGCACC TGAAGTCAGC CCCATACGAT

3701 ATAAGTTGTT AATTCTCATG TTTGACAGCT TATCATCGAT

*FIG. 5C*

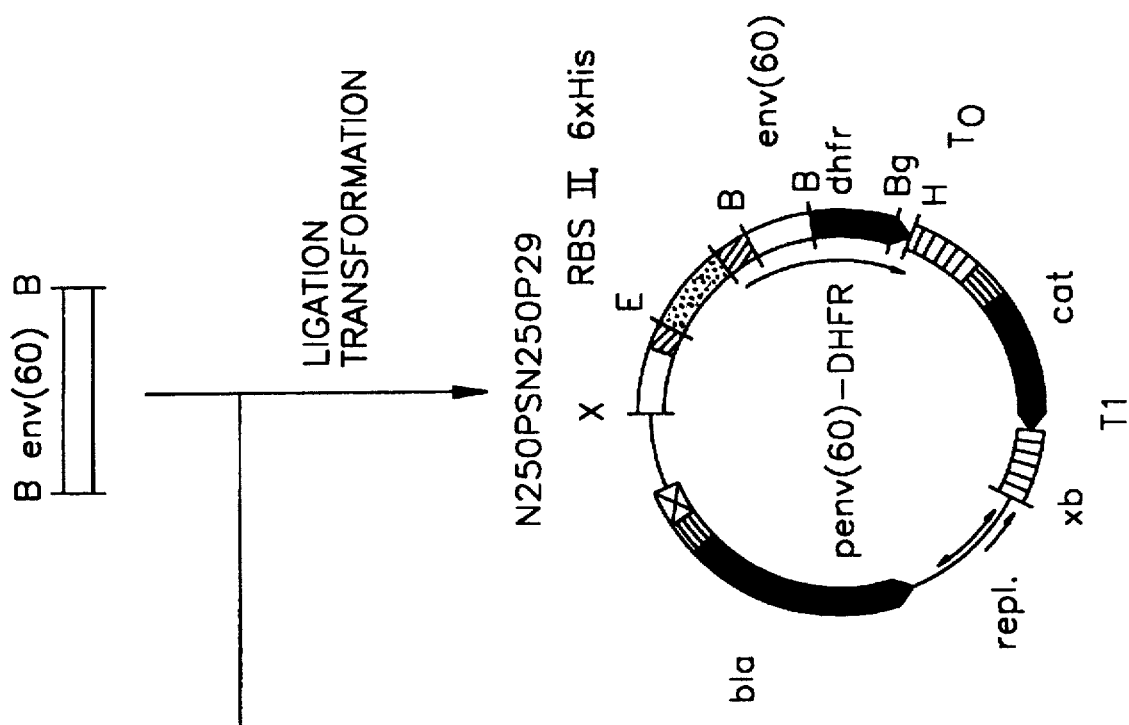
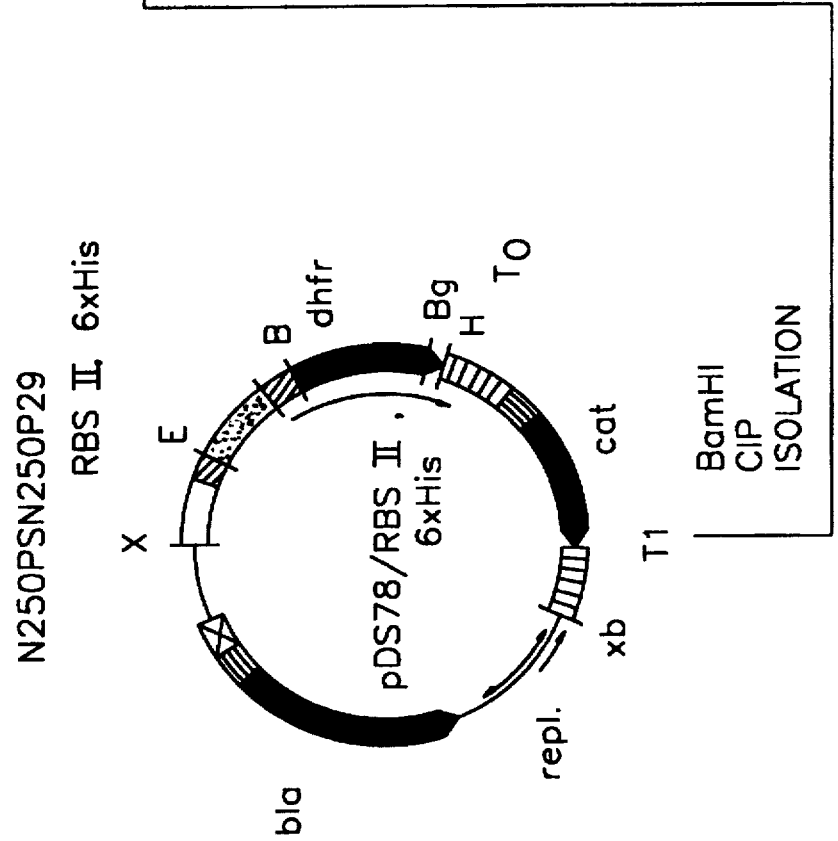
FIG. 8

```
              10         20         30         40         50
              |          |          |          |          |
   1 CTCGAGAAAT CATAAAAAAT TTATTTGCTT TGTGAGCGGA TAACAATTAT
  51 AATAGATTCA ATTGTGAGCG GATAACAATT TCACACAGAA TTCATTAAAG
 101 AGGAGAAATT AACTATGAGA GGATCCGTCG ACCTGCAGCC AAGCTTAATT
 151 AGCTGAGCTT GGACTCCTGT TGATAGATCC AGTAATGACC TCAGAACTCC
 201 ATCTGGATTT GTTCAGAACG CTCGGTTGCC GCCGGGCGTT TTTTATTGGT
 251 GAGAATCCAA GCTAGCTTGG CGAGATTTTC AGGAGCTAAG GAAGCTAAAA
 301 TGGAGAAAAA AATCACTGGA TATACCACCG TTGATATATC CCAATGGCAT
 351 CGTAAAGAAC ATTTTGAGGC ATTTCAGTCA GTTGCTCAAT GTACCTATAA
 401 CCAGACCGTT CAGCTGGATA TTACGGCCTT TTTAAAGACC GTAAAGAAAA
 451 ATAAGCACAA GTTTTATCCG GCCTTTATTC ACATTCTTGC CCGCCTGATG
 501 AATGCTCATC CGGAATTTCG TATGGCAATG AAAGACGGTG AGCTGGTGAT
 551 ATGGGATAGT GTTCACCCTT GTTACACCGT TTTCCATGAG CAAACTGAAA
 601 CGTTTTCATC GCTCTGGAGT GAATACCACG ACGATTTCCG GCAGTTTCTA
 651 CACATATATT CGCAAGATGT GGCGTGTTAC GGTGAAAACC TGGCCTATTT
 701 CCCTAAAGGG TTTATTGAGA ATATGTTTTT CGTCTCAGCC AATCCCTGGG
 751 TGAGTTTCAC CAGTTTTGAT TTAAACGTGG CCAATATGGA CAACTTCTTC
 801 GCCCCCGTTT TCACCATGGG CAAATATTAT ACGCAAGGCG ACAAGGTGCT
 851 GATGCCGCTG GCGATTCAGG TTCATCATGC CGTCTGTGAT GGCTTCCATG
 901 TCGGCAGAAT GCTTAATGAA TTACAACAGT ACTGCGATGA GTGGCAGGGC
 951 GGGGCGTAAT TTTTTAAGG CAGTTATTGG TGCCCTTAAA CGCCTGGGGT
1001 AATGACTCTC TAGCTTGAGG CATCAAATAA AACGAAAGGC TCAGTCGAAA
1051 GACTGGGCCT TTCGTTTTAT CTGTTGTTTG TCGGTGAACG CTCTCCTGAG
1101 TAGGACAAAT CCGCCGCTCT AGAGCTGCCT CGCGCGTTTC GGTGATGACG
1151 GTGAAAACCT CTGACACATG CAGCTCCCGG AGACGGTCAC AGCTTGTCTG
```

FIG. 12A

```
1201 TAAGCGGATG CCGGGAGCAG ACAAGCCCGT CAGGGCGCGT CAGCGGGTGT
1251 TGGCGGGTGT CGGGGCGCAG CCATGACCCA GTCACGTAGC GATAGCGGAG
1301 TGTATACTGG CTTAACTATG CGGCATCAGA GCAGATTGTA CTGAGAGTGC
1351 ACCATATGCG GTGTGAAATA CCGCACAGAT GCGTAAGGAG AAAATACCGC
1401 ATCAGGCGCT CTTCCGCTTC CTCGCTCACT GACTCGCTGC GCTCGGTCTG
1451 TCGGCTGCGG CGAGCGGTAT CAGCTCACTC AAAGGCGGTA ATACGGTTAT
1501 CCACAGAATC AGGGGATAAC GCAGGAAAGA ACATGTGAGC AAAAGGCCAG
1551 CAAAAGGCCA GGAACCGTAA AAGGCCGCG TTGCTGGCGT TTTTCCATAG
1601 GCTCCGCCCC CCTGACGAGC ATCACAAAAA TCGACGCTCA AGTCAGAGGT
1651 GGCGAAACCC GACAGGACTA TAAAGATACC AGGCGTTTCC CCCTGGAAGC
1701 TCCCTCGTGC GCTCTCCTGT TCCGACCCTG CCGCTTACCG GATACCTGTC
1751 CGCCTTTCTC CCTTCGGGAA GCGTGGCGCT TTCTCAATGC TCACGCTGTA
1801 GGTATCTCAG TTCGGTGTAG GTCGTTCGCT CCAAGCTGGG CTGTGTGCAC
1851 GAACCCCCCG TTCAGCCCGA CCGCTGCGCC TTATCCGGTA ACTATCGTCT
1901 TGAGTCCAAC CCGGTAAGAC ACGACTTATC GCCACTGGCA GCAGCCACTG
1951 GTAACAGGAT TAGCAGAGCG AGGTATGTAG GCGGTGCTAC AGAGTTCTTG
2001 AAGTGGTGGC CTAACTACGG CTACACTAGA AGGACAGTAT TTGGTATCTG
2051 CGCTCTGCTG AAGCCAGTTA CCTTCGGAAA AAGAGTTGGT AGCTCTTGAT
2151 CAGATTACGC GCAGAAAAAA AGGATCTCAA GAAGATCCTT TGATCTTTTC
2201 TACGGGGTCT GACGCTCAGT GGAACGAAAA CTCACGTTAA GGGATTTTGG
2251 TCATGAGATT ATCAAAAAGG ATCTTCACCT AGATCCTTTT AAATTAAAAA
2301 TGAAGTTTTA AATCAATCTA AGTATATAT GAGTAAACTT GGTCTGACAG
2351 TTACCAATGC TTAATCAGTG AGGCACCTAT CTCAGCGATC TGTCTATTTC
2401 GTTCATCCAT AGCTGCCTGA CTCCCCGTCG TGTAGATAAC TACGATACGG
2451 GAGGGCTTAC CATCTGGCCC CAGTGCTGCA ATGATACCGC GAGACCCACG
2501 CTCACCGGCT CCAGATTTAT CAGCAATAAA CCAGCCAGCC GGAAGGGCCG
```

FIG. 12B

2551 AGCGCAGAAG TGGTCCTGCA ACTTTATCCG CCTCCATCCA GTCTATTAAT

2601 TGTTGCCGGG AAGCTAGAGT AAGTAGTTCG CCAGTTAATA GTTTGCGCAA

2651 CGTTGTTGCC ATTGCTACAG GCATCGTGGT GTCACGCTCG TCGTTTGGTA

2701 TGGCTTCATT CAGCTCCGGT TCCCAACGAT CAAGGCGAGT TACATGATCC

2751 CCCATGTTGT GCAAAAAAGC GGTTAGCTCC TTCGGTCCTC CGATCGTTGT

2801 CAGAAGTAAG TTGGCCGCAG TGTTATCACT CATGGTTATG GCAGCACTGC

2851 ATAATTCTCT TACTGTCATG CCATCCGTAA GATGCTTTTC TGTGACTGGT

2901 GAGTACTCAA CCAAGTCATT CTGAGAATAG TGTATGCGGC GACCGAGTTG

2951 CTCTTGCCCG GCGTCAATAC GGGATAATAC CGCGCCACAT AGCAGAACTT

3001 TAAAAGTGCT CATCATTGGA AAACGTTCTT CGGGGCGAAA ACTCTCAAGG

3051 ATCTTACCGC TGTTGAGATC CAGTTCGATG TAACCCACTC GTGCACCCAA

3101 CTGATCTTCA GCATCTTTTA CTTTCACCAG CGTTTCTGGG TGAGCAAAAA

3151 CAGGAAGGCA AAATGCCGCA AAAAAGGGAA TAAGGGCGAC ACGGAAATGT

3201 TGAATACTCA TACTCTTCCT TTTTCAATAT TATTGAAGCA TTTATCAGGG

3251 TTATTGTCTC ATGAGCGGAT ACATATTTGA ATGTATTTAG AAAAATAAAC

3301 AAATAGGGGT TCCGCGCACA TTTCCCCGAA AAGTGCCACC TGACGTCTAA

3351 GAAACCATTA TTATCATGAC ATTAACCTAT AAAAATAGGC GTATCACGAG

3401 GCCCTTTCGT CTTCAC

FIG. 12C

```
            10        20        30        40        50
             |         |         |         |         |
   1 GAGCTCTCTCGACGCAGGACTCGGCTTGCTGAAGCGCGCACGGCAAGAGG
  51 CGAGGGGGGGCGACTGGTGAGTACGCCAAAAATTTTGACTAGCGGAGGCT
 101 AGAAGGAGAGAGATGGGTGCGAGAGCGTCAGTATTAAGCGGGGGAAAATT
 151 AGATCGATGGGAAAAAATTCGGTTAAGGCCAGGGGGAAAGAAAAAATATA
 201 AATTAAAACATATAGTATGGGCAAGCAGGGAGCTAGAACGATTCGCAGTT
 251 AATCCTGGCCTGTTAGAAACATCAGAAGGCTGTAGACAAATACTGGGACA
 301 GCTACAACCATCCCTTCAGACAGGATCAAAAGAACTTAGATCATTATATA
 351 ATACAGTAGCAACCCTCTATTGTGTGCATCAAAGGATAGAGATAAAAGAC
 401 ACCAAGGAAGCTTTAGACAAGATAGAGGAAGAGCAAAACAAAAGTAAGAA
 451 AAAAGCACAGCAAGCAGCAGCTGACACAGGACACAGCAGCCAGGTCAGCC
 501 AAAATTACCCTATAGTGCAGAACATCCAGGGGCAAATGGTACATCAGGCC
 551 ATATCACCTAGAACTTTAAATGCATGGGTAAAAGTAGTAGAAGAGAAGGC
 601 TTTCAGCCCAGAAGTGATACCCATGTTTTCAGCATTATCAGAAGGAGCCA
 651 CCCCACAAGATTTAAACACCATGCTAAACACAGTGGGGGGACATCAAGCA
 701 GCCATGCAAATGTTAAAAGAGACCATCAATGAGGAAGCTGCAGAATGGGA
 751 TAGAGTGCATCCAGTGCATGCAGGGCCTATCGCACCAGGCCAGATGAGAG
 801 AACCAAGGGGAAGTGACATAGCAGGAACTACTAGTACCCTTCAGGAACAA
 851 ATAGGATGGATGACAAATAATCCACCTATCCCAGTAGGAGAAATTTATAA
 901 AAGATGGATAATCCTGGGATTAAATAAATAGTAAGAATGTATAGCCCTA
 951 CCAGCATTCTGGACATAAGACAAGGACCAAAAGAACCCTTTAGAGACTAT
1001 GTAGACCGGTTCTATAAAACTCTAAGAGCCGAGCAAGCTTCACAGGAGGT
1051 AAAAAATTGGATGACAGAAACCTTGTTGGTCCAAAATGCGAACCCAGATT
1101 GTAAGACTATTTTAAAAGCATTGGGACCAGCGGCTACACTAGAAGAAATG
1151 ATGACAGCATGTCAGGGAGTAGGAGGACCCGGCCATAAGGCAAGAGTTTT
1201 GGCTGAAGCAATGAGCCAAGTAACAAATTCAGCTACCATAATGATGCAGA
1251 GAGGCAATTTTAGGAACCAAAGAAGATTGTTAAGTGTTTCAATTGTGGC
1301 AAAGAAGGGCACACAGCCAGAATTGCAGGGCCCTAGGAAAAAGGGCTG
1351 TTGGAAATGTGGAAGGAAGGACACCAAATGAAAGATTGTACTGAGAGAC
1401 AGGCTAATTTTTTAGGGAAGATCT
```

FIG. 16

```
           10         20         30         40         50
            |          |          |          |          |
   1 AAGCTTTAGA CAAGGTAGAG GAAGAGCAAA ACAACAGTAA GAAAAAGGCA

51 CAGCAAGAAG CAGCTGACGC AGGAAACAGA AACCAGGTCA GCCAAAATTA

101 CCCTATAGTG CAAAACCTAC AGGGACAAAT GGTACATCAG GCCATATCAC

151 CTAGAACTTT AAATGCATGG GTAAAAGTAG TGGAAGAGAA GGCTTTCAGC

201 CCAGAAGTAA TACCCATGTT TTCAGCATTA TCAGAAGGAG CCACCCCACA

251 AGATTTAAAC ACCATGCTAA ACACAGTGGG GGGACATCAA GCAGCCATGC

301 AAATGTTAAA AGAAACCATC AATGAGGAAG CTGCAGAATG GGATAGATTG

351 CACCCAGTGC ATGCAGGGCC TATTGCACCA GGCCAGATGA GAGAACCAAG

401 GGGAAGTGAC ATAGCAGGAA CTACTAGTAC CCTTCAGGAA CAAATAGGAT

451 GGATGACAAA TAATCCACCT ATCCCAGTAG GAGAAATATA TAAGAGATGG

501 ATAATCCTGG GATTAAATAA AATAGTAAGA ATGTATAGCC CTACCAGCAT

551 TCTGGATATA AAACAAGGAC CAAAAGAACC CTTTAGAGAT TATGTAGACC

601 GGTTCTATAA AACCCTAAGA GCCGAGCAAG CTACACAGGA AGTAAAAAAT

651 TGGATGACAG AAACCTTGTT GGTCCAAAAT GCGAATCCAG ATTGTAAGAC

701 TATTTTAAAA GCATTAGGAC CAGCAGCTAC ACTAGAAGAA ATGATGACAG

751 CATGTCAGGG AGTGGGGGGA CCCGGCCATA AAGCAAGAGT TTTGGCTGAA

801 GCAATGAGCC AAGTAACAGG TTCAGCTGCC ATAATGATGC AGAGAGGCAA

851 TTTTAGGAAC CAAAGAAAGA CTGTTAAGTG TTTCAATTGT GGCAAAGAAG

901 GGCACATAGC CAGAAATTGC AGGGCCCCTA GGAAAAAGGG CTGTTGGAAA

951 TGTGGAAAGG AAGGACATCA AATGAAGGAT GCACAGAAA  GACAGGCTAA

1001 TTTTTTAGGG AAGATCTGGC CTTCCCACAA GGGGAGGCCA GGAAATTTTC

1051 TTCAGAGCAG ACCAGAGCCA ACAGCCCCAC CAGAAGAGAG CTTCAGGTTT

1101 GGGGAAGCAA CAGCTCCCTC TCAGAAGCAG GAGCCGATAG ACAAGGAACT

1151 GTATCCCTTA GCCTCCCTCA AATCACTCTT TGGCAGCGAC CCCTCGTCAC
```

*FIG. 17A*

```
1201 AATAAAGATA GGGGGGCAAC TAAAGGAAGC TCTATTAGAT ACAGGAGCAG
1251 ATGATACAGT AGTAGAAGAA ATGAGTTTGC CAGGAAGATG GAAACCAAAA
1301 ATGATAGGAG GAATTGGAGG TTTTATCAAA GTAAGACAGT ATGATCAGAT
1351 ACTCGTAGAA ATCTGTGGAC ATAAAGCTAT AGGTACAGTA TTAGTAGGAC
1401 CTACACCTGT CAACATAATT GGAAGAAATC TGTTGACTCA GATTGGTTGC
1451 ACTTTAAATT TTCCCATTAG TCCTATTGAA ACTGTACCAG TAAAATTAAA
1501 GCCAGGAATG GATGGCCCAA AAGTTAAACA ATGGCCATTG ACAGAAGAAA
1551 AAATAAAAGC ATTAATAGAA ATTTGTACAG AAATGGAAAA GGAAGGGAAA
1601 ATTTCAAAAA TTGGGCCTGA AAATCCATAC AATACTCCAG TATTTGCCAT
1651 AAAGAAAAAG GACAGTACTA AATGGAGAAA ATTAGTAGAT TTCAGAGAAC
1701 TTAATAAAAG AACTCAAGAT TTCTGGGAAG TTCAATTAGG AATACCACAT
1751 CCCGCAGGGT TAAAAAAGAA AAAATCAGTA ACAGTCCTGG ATGTGGGTGA
1801 TGCATATTTT TCAGTTCCCC TAGATAAAGA CTTCAGAAAA TATACTGCAT
1851 TTACCATACC TAGTATAAAC AATGAGACAC CAGGGATTAG ATATCAGTAC
1901 AATGTGCTTC CACAGGGATG GAAAGGATCA CCAGCAATAT TCCAAAGTAG
1951 CATGACAAAA ATCTTAGAGC CTTTTAGAAA ACAAAATCCA GACATAGTTA
2001 TCTATCAATA CATGGATGAT TTGTATGTAG GATCTGACTT AGAAATAGAG
2051 CAGCATAGAA CAAAAATAGA GGAACTGAGA CAGCATCTGT TGAAGTGGGG
2101 ATTTACCACA CCAGACAAAA AACATCAGAA AGAACCTCCA TTCCTTTGGA
2151 TGGGTTATGA ACTCCATCCT GATAAATGGA CAGTACAGCC TATAGTGCTG
2201 CCAGAAAAAG ACAGCTGGAC TGTCAATGAC ATACAGAAGT TAGTGGGAAA
2251 ATTGAATTGG GCAAGTCAGA TTTATGCAGG GATTAAAGTA AAGCAATTAT
2301 GTAAGCTACT TAGGGGACCC AAAGCACTAA CAGAAGTAAT ACCACTAACA
2351 AAAGAAGCAG AGCTAGAACT AGCAGAAAAC AGGGAGATTC TAAAAGAACC
2401 AGTACATGGA GTGTATTGTG ACCCATCAAA AGACTTAGTA GCAGAAATAC
2451 AGAAGCAGGG GGAAGGCCAA TGGACATATC AAATTTATCA AGAACCATTT
2501 AAGAATCTGA AAACAGGAAA GTATGCAAGA ATGAGGGGTG CCCACACTAA
2551 TGATATAAAA CAGTTAACAG AGGCAGTGCA AAAAATAGCC ACAGAAGGCA
```

FIG. 17B

```
2601 TAGTAATATG GGGAAAGACT CCTAAATTTA GACTACCCAT ACAAAAGGAA
2651 ACATGGGAAG CATGGTGGAC GGAGTATTGG CAAGCCACCT GGATTCCTGA
2701 GTGGGAGTTT GTCAATACCC CTCCCTTAGT GAAATTATGG TACCAGTTAG
2751 AGAAAGAACC CATAGTAGGA GCAGAAACTT TCTATGTAGA TGGGGCAGCT
2801 AATAGGGAGA CTAAATTAGG AAAAGCAGGA TATGTTACTG ACAGGGGAAG
2851 ACAAAAAGTT GTCTCCCTAA ATGACACAAC AAATCAGAAG ACTGAGTTAC
2901 AAGCAATTCA TCTAGCTTTG CAGGATTCGG GACTAGAAGT AAACATAGTA
2951 ACAGACTCAC AATATGCATT AGGAATCATT CAAGCACAAC CAGATAAAAG
3001 TGAATCAGAG TTAGTCAGTC AAATAATAGA GCAGTTAATA AAAAGGAAA
3051 AGGTCTACCT GGCATGGGTA CCAGCACACA AAGGAATTGG AGGAAATGAA
3101 CAAGTAGATA AATTAGTCAG TGCTGGAATC AGAAAAGTAC TATTTTTAGA
3151 TGGAATAGAT AAGGCCCAAG AAGACCATGA GAAATATCAC AGTAATTGGA
3201 GAGCAATGGC TAATGATTTT AACCTGCCAC CTGTAGTAGC AAAAGAAATA
3251 GTAGCCAGCT GTGATAAATG TCAGCTAAAA GGAGAAGCCA TGCATGGACA
3301 AGTAGACTGT AGTCCAGGAA TATGGCAACT AGATTGTACA CATTTAGAAG
3351 GAAAAATTAT CCTGGTAGCA GTTCATGTAG CTAGTGGATA TATAGAAGCA
3401 GAAGTCATTC CAGTAGAGAC AGGGCAGGAA ACAGCATATT TTCTCTTAAA
3451 ATTAGCAGGA AGATGGCCAG TAAAAACAGT ACATACAGAC AATGGCCCTA
3501 ATTTCACCAG TACTACGGTT AAGGCCGCCT GTTGGTGGGC AGGGATCAAG
3551 CAGGAATTTG GCATTCCCTA CAATCCCCAA AGTCAAGGGG TAGTAGAATC
3601 TATGAATAAA GAGTTAAAGA AAATTATAGG ACAGGTAAGA GATCAGGCTG
3651 AACATCTTAA GACAGCAGTA CAAATGGCAG TATTCATCCA CAATTTTAAA
3701 AGAAAAGGGG GGATTGGGGG GTACAGTGCA GGGGAAAGAA TAGTAGACAT
3751 AATAGCAACA GACATACAAA CTAAAGAATT ACAAAAACAA ATTACAAAAA
3801 TTCAAAATTT TCGGGTTTAT TACAGGGACA GCAGAGAACC ATTTTGGAAA
3851 GGACCAGCAA AGCTT
```

FIG. 17C

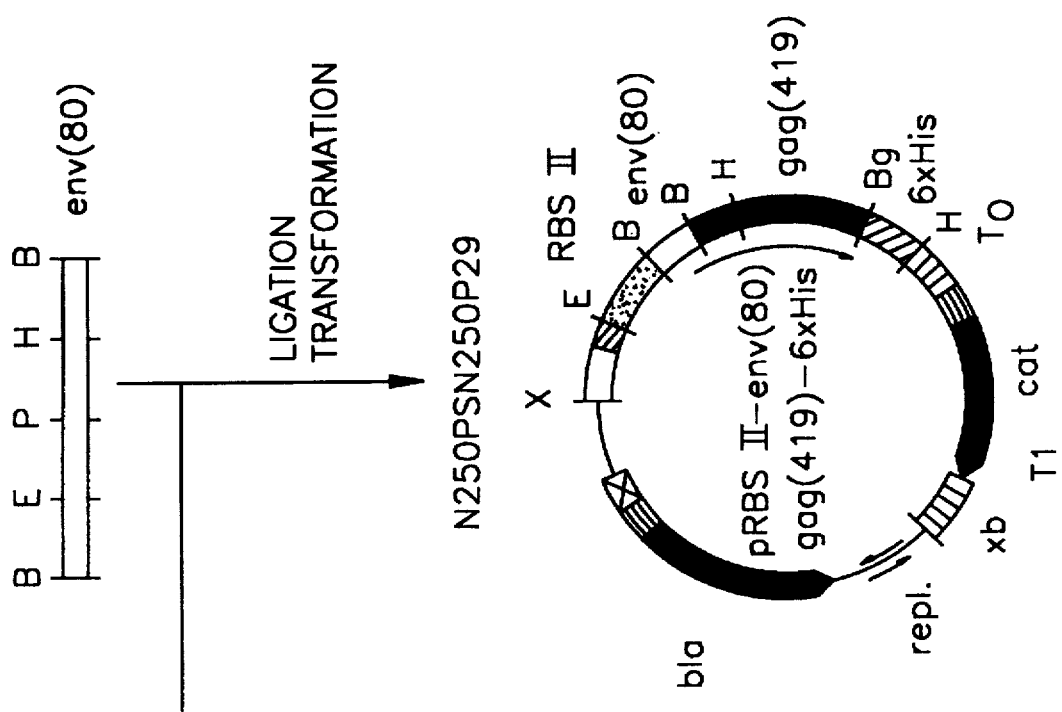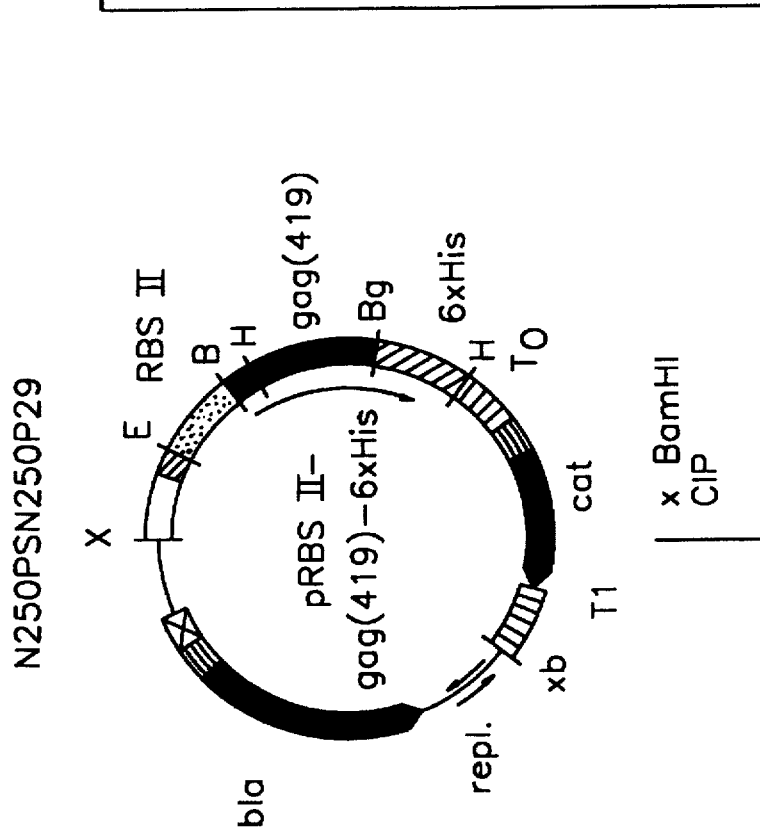
FIG. 19

HIV-2 ENVELOPE POLYPEPTIDES

This is a continuation of application Ser. No. 08/213,416 filed Mar. 15, 1994, which is a continuation of Ser. No. 07/895,977, filed Jun. 9, 1992, now abandoned, which is a continuation of Ser. No. 07/268,322, filed Nov. 7, 1988, now abandoned.

TECHNICAL FIELD

The present invention relates to novel polypeptides comprising at least one antigenic and/or immunogenic determinant of the envelope protein (env) of the HIV-2 virus, DNA sequences which code for these polypeptides, recombinant vectors which contain these DNA sequences, microorganisms transformed with these recombinant vectors and processes for the production of the polypeptides by recombinant DNA technology. The invention also relates to a method for the detection of HIV antibodies (HIV-2 antibodies or HIV-1 and HIV-2 antibodies) or HIV viruses (HIV-2 viruses or HIV-1 and HIV-2 viruses) in human serum or other biological body fluids.

BACKGROUND OF THE INVENTION

In 1986 a new virus designated as HIV-2 was isolated from West African AIDS patients [Clavel et al., Science 233, 343–346 (198); Clavel et al., Nature 324, 691–695 (1986)]. On the basis of its morphology, its lymphotropism and its cytophatic in vitro activity on $T_4$-positive cells, this virus was associated with the AIDS-causing HIV-1 viruses. In spite of these similiar properties, a genetic comparison of HIV-1 and HIV-2 viruses showed, however, only a limited sequence homology [Guyader et al., Nature 326, 662–669 (1987)].

More than 20 different HIV-2 viruses have been isolated from West African AIDS patients and from European AIDS patients [Guyader et al., supra; Brun-Vezinet et al., Lancet 1, 128–132 (1987)]. The sera of these AIDS patients were all negative in the HIV-1 ELISA [Brun-Vezinet et al., supra]. Accordingly, there is a very great need for a precise and rapid method for the diagnosis of HIV-2 viruses in human blood and in other body fluids.

SUMMARY OF THE INVENTION

Accordingly, novel polypeptides having amino acid sequences which correspond to at least one antigenic and/or immunogenic determinant of the envelope protein (env) of the HIV-2 virus have been produced by using recombinant DNA techniques. These polypeptides permit the detection of HIV-2 antibodies or HIV-2 viruses or fragments thereof in human sera or other biological body fluids.

The present invention provides such polypeptides. More precisely, the invention provides polypeptides having the amino acid sequence SerAlaArgLeuAsnSerTrpGlyCysAlaPheArgGlnValCysHisThr (I)
ThrValProTrpValAsnAspSerLeuAlaProAspTrpAspAsnMet
ThrTrpGlnGluTrpGluLysGlnValArgTyrLeuGluAlaAsnIleSer
LysSerLeuGluGlnAlaGlnGly (ENV(60))

or subsequences or functional equivalents thereof which correspond to at least one antigenic and/or immunogenic determinant of the HIV-2 env protein.

The invention also provides the previously defined polypeptides, fragments and functional equivalents which are additionally covalently linked to an affinity peptide and a carrier polypeptide. The previously defined polypeptides which are additionally covalently linked with an affinity peptide and a polypeptide whose amino acid sequence corresponds to at least one antigenic and/or immunogenic determinant of the HIV-1 envelope protein (env) and/or of the HIV-1 core protein (gag) are also provided. Since such fusion proteins have antigenic and/or immunogenic determinants of both HIV-1 viruses and HIV-2 viruses, they can be used as an effective diagnostic tool for the simultaneous detection of HIV-1 and HIV-2 antibodies or HIV-1 and HIV-2 viruses or fragments thereof in human sera or other biological body fluids.

The preferred polypeptides of the present invention are defined by the general formulae

A - B - C

A - C - B and

C - B - A wherein

A is an affinity peptide,

B is a polypeptide having the amino acid sequence of formula I and

C is a carrier polypeptide or a polypeptide, the amino acid sequence of which corresponds to at least one antigenic and/or immunogenic determinant of the HIV-1 envelope protein (env) and/or the HIV-1 core protein (gag). The latter polypeptide will hereinafter be referred to as an "HIV-1 polypeptide."

Especially preferred polypeptides are those having the formula

MetArgGlySerHisHisHisHisHisHisGlySerAlaArgLeuAsnSerTrp (II)
GlyCysAlaPheArgGlnValCysHisThrThrValProTrpValAsnAspSer
LeuAlaProAspTrpAspAsnMetThrTrpGlnGluTrpGluLysGlnValArg
TyrLeuGluAlaAsnIleSerLysSerLeuGluGlnAlaGlnGlySerGlyIle
MetValArgProLeuAsnCysIleValAlaValSerGlnAsnMetGlyIleGly
LysAsnGlyAspLeuProTrpProProLeuArgAsnGluPheLysTyrPheGln
ArgMetThrThrThrSerSerValGlyGlyLysGlnAsnLeuValIleMetGly
ArgLysThrTrpPheSerIleProGluLysAsnArgProLeuLysAspArgIle
AsnIleValLeuSerArgGluLeuLysGluProProArgGlyAlaHisPheLeu
AlaLysSerLeuAspAspAlaLeuArgLeuIleGluGlnProGluLeuAlaSer
LysValAspMetValTrpIleValGlyGlySerSerValTyrGlnGluAlaMet
AsnGlnProGlyHisLeuArgLeuPheValThrArgIleMetGlnGluPheGlu
SerAspThrPhePheProGluIleAspLeuGlyLysTyrLysLeuLeuProGlu
TyrProGlyValLeuSerGluValGlnGluGluLysGlyIleLysTyrLysPhe
GluValTyrGluLysLysGlySerArgSerValAsnLeuVal
(ENV(60)-DHFR)

MetArgGlySerHisHisHisHisHisHisGlySerGlyIleMetValArgPro (III)
LeuAsnCysIleValAlaValSerGlnAsnMetGlyIleGlyLysAsnGlyAsp
LeuProTrpProProLeuArgAsnGluPheLysTyrPheGlnArgMetThrThr
ThrSerSerValGlyGlyLysGlnAsnLeuValIleMetGlyArgLysThrTrp
PheSerIleProGluLysAsnArgProLeuLysAspArgIleAsnIleValLeu
SerArgGluLeuLysGluProProArgGlyAlaHisPheLeuAlaLysSerLeu
AspAspAlaLeuArgLeuIleGluGlnProGluLeuAlaSerLysValAspMet
ValTrpIleValGlyGlySerSerValTyrGlnGluAlaMetAsnGlnProGly
HisLeuArgLeuPheValThrArgIleMetGlnGluPheGluSerAspThrPhe
PheProGluIleAspLeuGlyLysTyrLysLeuLeuProGluTyrProGlyVal
LeuSerGluValGlnGluGluLysGlyIleLysTyrLysPheGluValTyrGlu
LysLysGlySerArgSerAlaArgLeuAsnSerTrpGlyCysAlaPheArgGln
ValCysHisThrThrValProTrpValAsnAspSerLeuAlaProAspTrpAsp
AsnMetThrTrpGlnGluTrpGluLysGlnValArgTyrLeuGluAlaAsnIle
SerLysSerLeuGluGlnAlaGlnGlySerValAsnLeuVal
(DHFR-ENV(60))

-continued or

MetArgGlySerGluAlaGlnGlnHisLeuLeuGlnLeuThrValTrpGlyIle  (IV)
LysGlnLeuGlnAlaArgIleLeuAlaValGluArgTyrLeuLysAspGlnGln
LeuLeuGlyIleTrpGlyCysSerGlyLysLeuIleCysThrThrAlaValPro
TrpAsnAlaSerTrpSerAsnLysLeuLeuGluGlnIleTrpAsnAsnMetThr
TrpMetGluTrpAspArgGluIleAsnAsnTyrThrGlySerGlyIleArgLeu
ArgProGlyGlyLysLysTyrLysLeuLysHisIleValTrpAlaSerArg
GluLeuGluArgPheAlaValAsnProGlyLeuLeuGluThrSerGluGlyCys
ArgGlnIleLeuGlyGlnLeuGlnProSerLeuGlnThrGlySerLysGluLeu
ArgSerLeuTyrAsnThrValAlaThrLeuTyrCysValHisGlnArgIleGlu
IleLysAspThrLysGluAlaLeuAspLysValGluGluGluGlnAsnAsnSer
LysLysLysAlaGlnGlnGluAlaAlaAspAlaGlyAsnArgAsnGlnValSer
GlnAsnTyrProIleValGlnAsnLeuGlnGlyGlnMetValHisGlnAlaIle
SerProArgThrLeuAsnAlaTrpValLysValValGluGluLysAlaPheSer
ProGluValIleProMetPheSerAlaLueSerGluGlyAlaThrProGlnAsp
LeuAsnThrMetLeuAsnThrValGlyGlyHisGlnAlaAlaMetGlnMet
LeuLysGluThrIleAsnGluGluAlaAlaGluTrpAspArgLeuHisProVal
HisAlaGlyProIleAlaProGlyGlnMetArgGluProArgGlySerAspIleAla
GlyThrThrSerThrLeuGlnGluGlnIleGlyTrpMetThrAsnAsnProPro
IleProValGlyGluIleTyrLysArgTrpIleIleLeuGlyLeuAsnLysIle
ValArgMetTyrSerProThrSerIleLeuAspIleLysGlnGlyProLysGlu
ProPheArgAspTyrValAspArgPheTyrLysThrLeuArgAlaGluGlnAla
ThrGlnGluValLysAsnTrpMetThrGluThrLeuLeuValGlnAsnAlaAsn
ProAspCysLysThrIleLeuLysAlaLeuGlyProAlaAlaThrLeuGluGlu
MetMetThrAlaCysGlnGlyValGlyGlyProGlyHisLysAlaArgValLeu
AlaGluAlaMetSerGlnValThrGlySerAlaAlaIleMetMetGlnArgGly
AsnPheArgAsnGlnArgLysThrValLysCysPheAsnCysGlyLysGluGly
HisIleAlaArgAsnCysArgAlaProArgLysLysGlyCysTrpLysCysGly
LysGlyHisGlnMetLysAspCysThrGluArgGlnAlaAsnPheLeu
GlyLysIleGlyArgSerAlaArgLeuAsnSerTrpGlyCysAlaPheArgGln
ValCysHisThrThrValProTrpValAsnAspSerLeuAlaProAspTrpAsp
AsnMetThrTrpGlnGluTrpGluLysGlnValArgTyrLeuGluAlaAsnIle
SerLysSerLeuGluGlnAlaGlnGlySerHisHisHisHisHisHis
ENV(80)-GAG(419)-ENV(60)).

BRIEF DESCRIPTION OF THE FIGURES

The present invention can be more readily understood by reference to the accompanying Figures, in which the following abbreviations and symbols are used:

B, Bg, E, H, Sa, X and Xb denote cleavage sites for the restriction enzymes BamHI, BglII, EcoRI, HindIII, PstI, SalI, XhoI and XbaI, respectively.

▭ represents the promoters of the genes bla, lacI and neo; ▭ represents the ribosomal binding sites of the genes bla, cat, neo and lacI; ▭ represents the terminators $t_0$ and T1; ▭ represents the regulatable promoter/operator element N25OPSN25OP29; ▭ represents the ribosomal binding site RBSII;→ represents the coding region under control of this ribosomal binding site; ▬ represents the regions which code for the six histidines; ⇨ represents the region which is required for the replication (repl.);

▬▶ represents coding regions for dihydrofolate reductase (dhfr), chloramphenicol acetyltransferase, lac repressor (lacI), β-lactamase (bla) and neomycin phosphotransferase (neo); ▭ represents the synthetic env(60) gene; ▬ represents HIV-1 gene fragments.

The contents of the figures can be summarized as follows:

FIG. 1 Representation of the nucleotide sequence of the synthetic env(60) gene and the amino acid sequence of the ENV(60) polypeptide derived therefrom. The individual oligonucleotide fragments from which the synthetic env(60) gene is constructed are denoted by the numbers 1–14.

Figure 2:
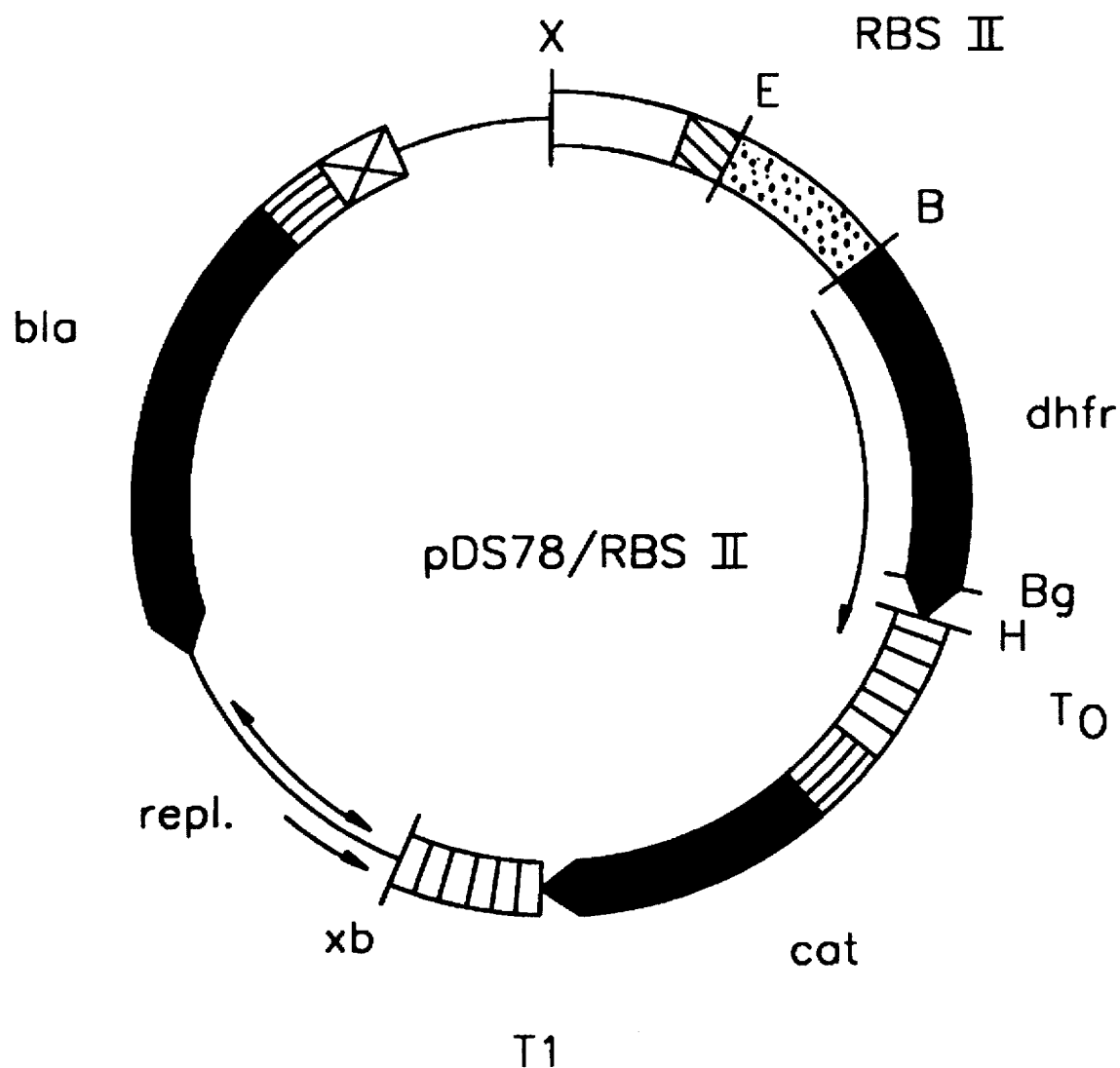

FIG. 2 Schematic representation of plasmid pDS78/RBSII.

FIG. 3 Nucleotide sequence of the plasmid pDS78/RBSII. In the sequence the recognition sites for the restriction enzymes set forth in FIG. 2 are overlined, while the regions coding for β-lactamase and dihydrofolate reductase are underlined.

Figure 4:
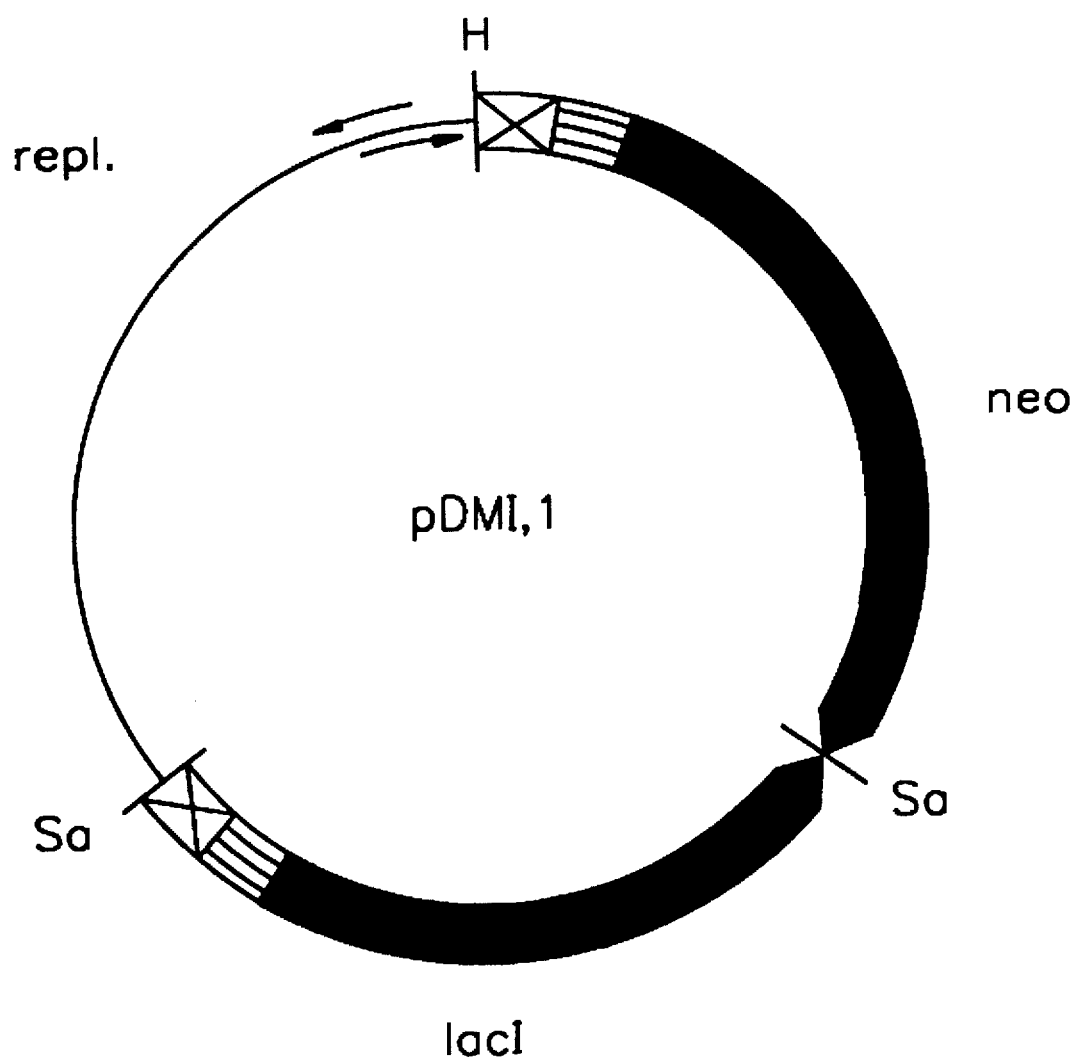

FIG. 4 Schematic representation of plasmid pDMI.1.

FIG. 5A through FIG. 5C Nucleotide sequence of plasmid pDMI.1. In the sequence the recognition sites for the restriction enzymes set forth in FIG. 4 are overlined, while the regions coding for neomycin phosphotransferase and lac repressor are underlined.

Figure 6:
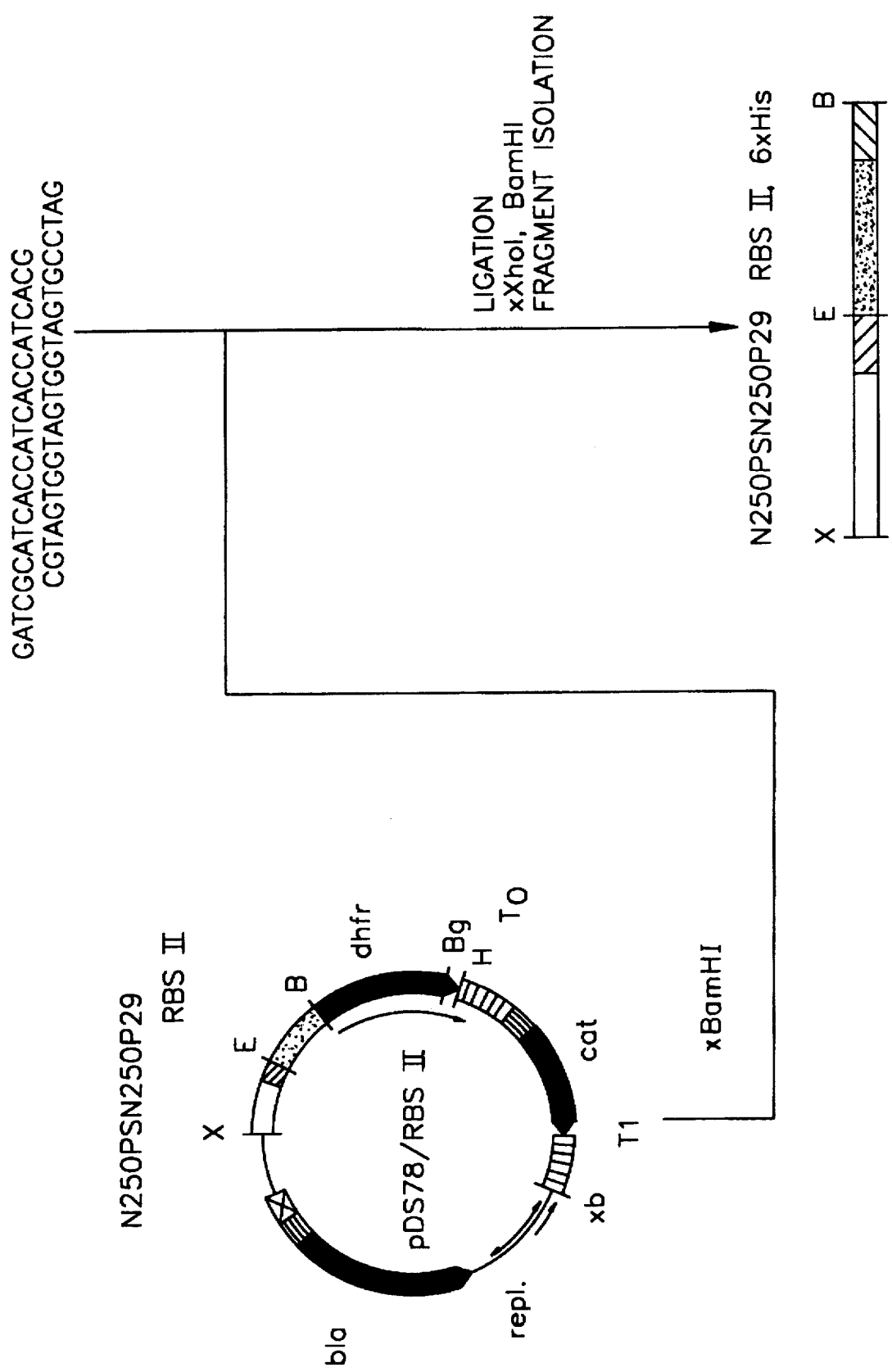

FIG. 6 Schematic representation of the production of the XhoI/BamHI fragment containing the regularable promoter/operator element N25OPBN25OP29, the ribosomal binding site RBSII and the region coding for six histidines.

Figure 7:
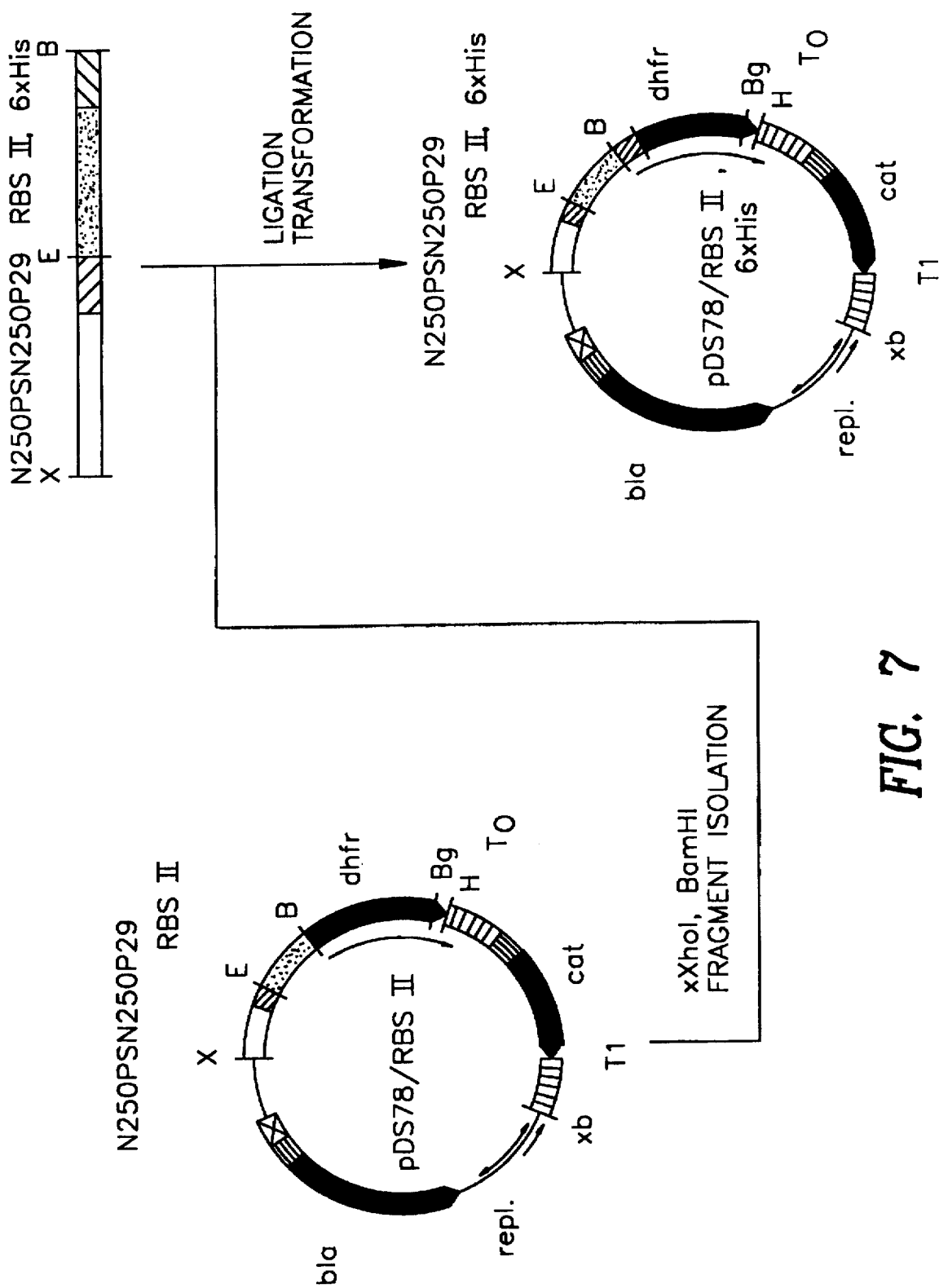

FIG. 7 Schematic representation of the construction of plasmid pDS78/RBSII,6xHis using the plasmid pDS78/RBSII and the XhoI/BamHI fragment containing the regularable promoter/operator element N25OPSN25OP29, the ribosomal binding site RBSII and the region coding for six histidines.

FIG. 8 Schematic representation of the construction of plasmid penv(60)-DHFR.

Figure 9:
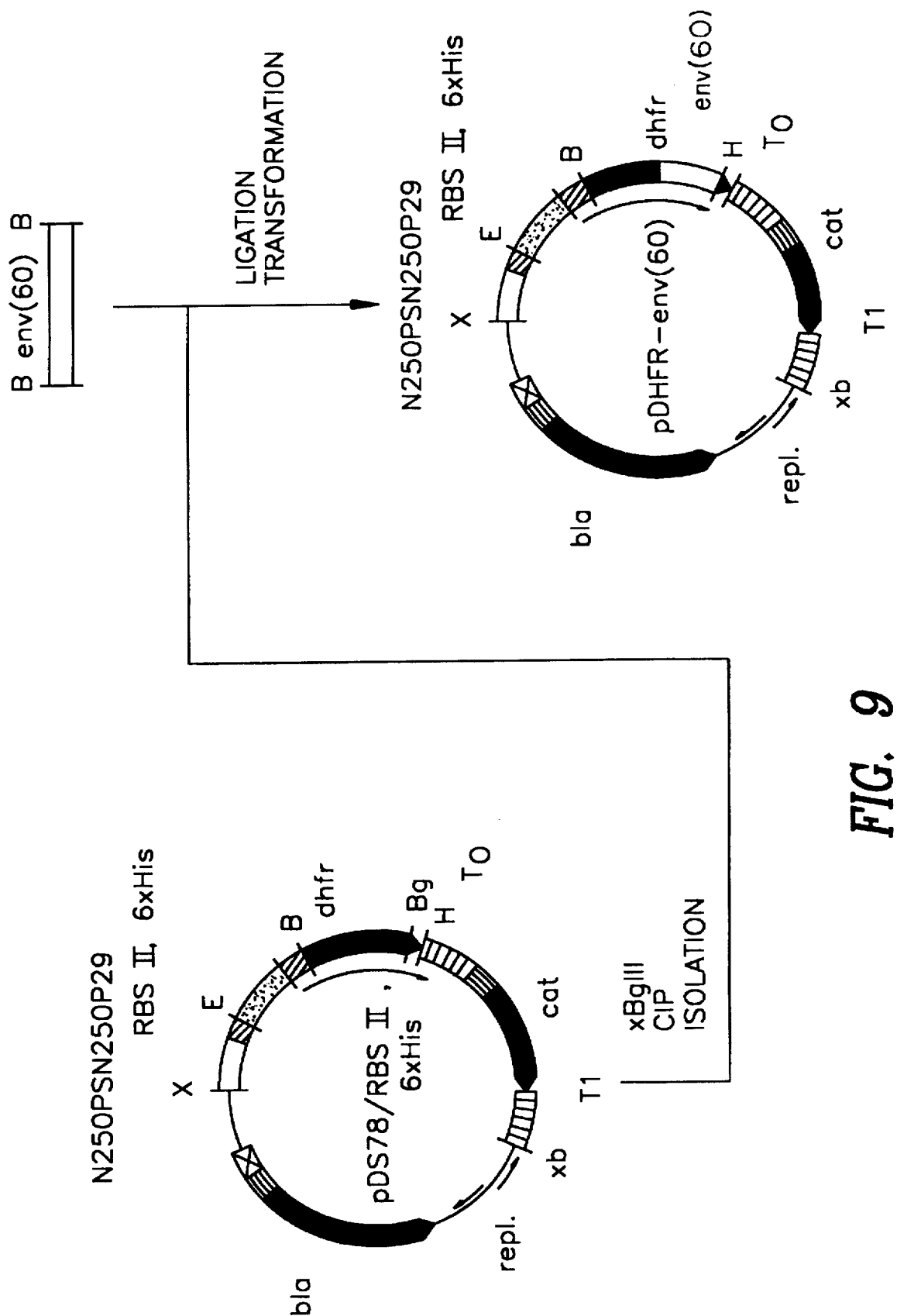

FIG. 9 Schematic representation of the construction of plasmid pDHFR-env(80).

Figure 10:
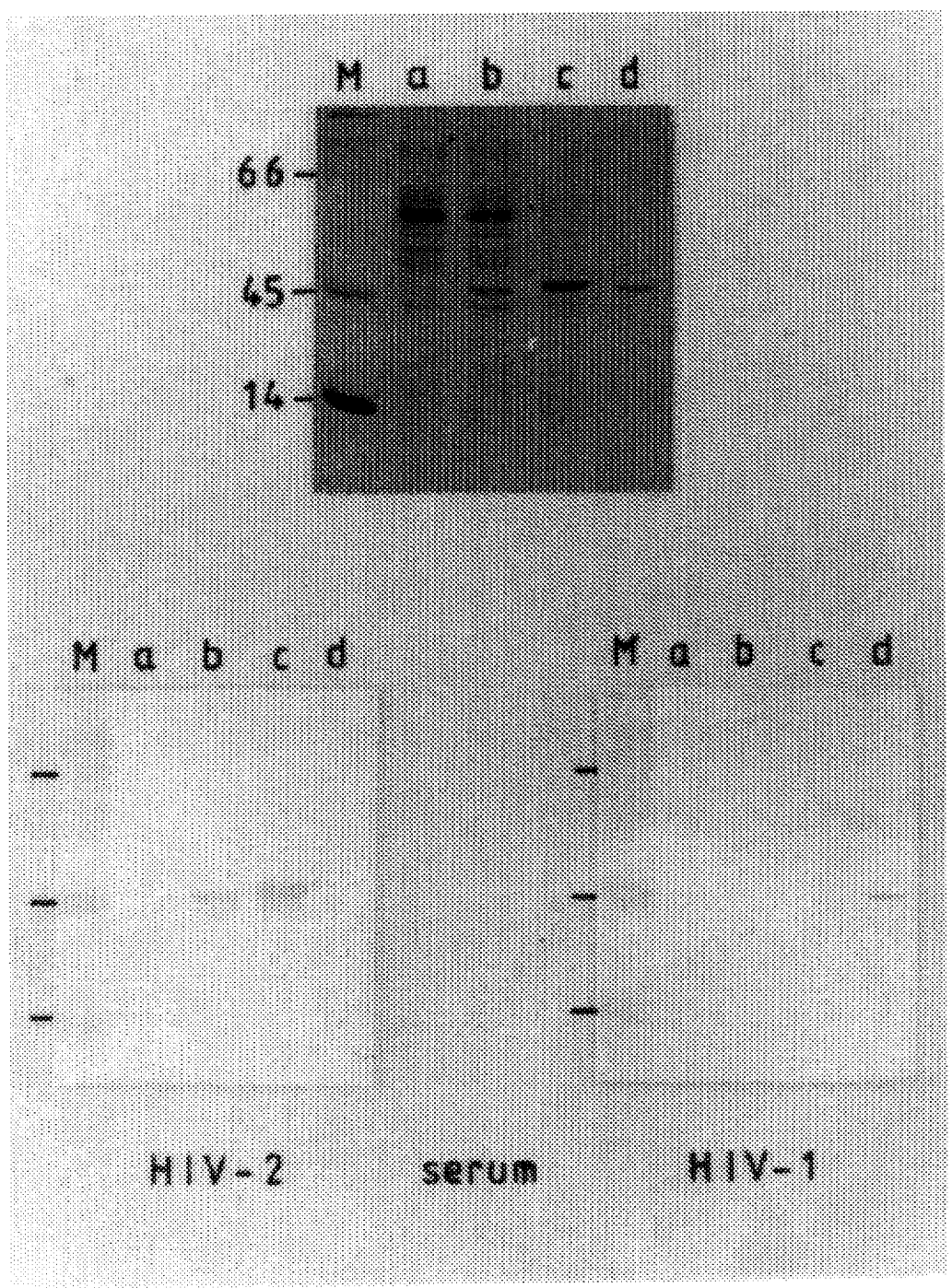

FIG. 10 Reactivity of the ENV(60)-DHFR and DHFR-ENV(60) polypeptides with HIV-positive sera.

The upper part shows the electrophoretic analysis of *E. coli* M15 lysates containing plasmids PDS78/RSBII,6xHis (trace a), penv(60)-DHFR (trace b) and pDHFR-env(60) (trace c). Trace d contains purified HIV-1 ENV(80)-DHFR. The lower part shows the corresponding immunoblots which were produced with HIV-2 (left) and HIV-1 (right) positive serum. The M traces contain pre-stained molecular weight standards, the sizes of which are given in kilodaltons.

Figure 11:
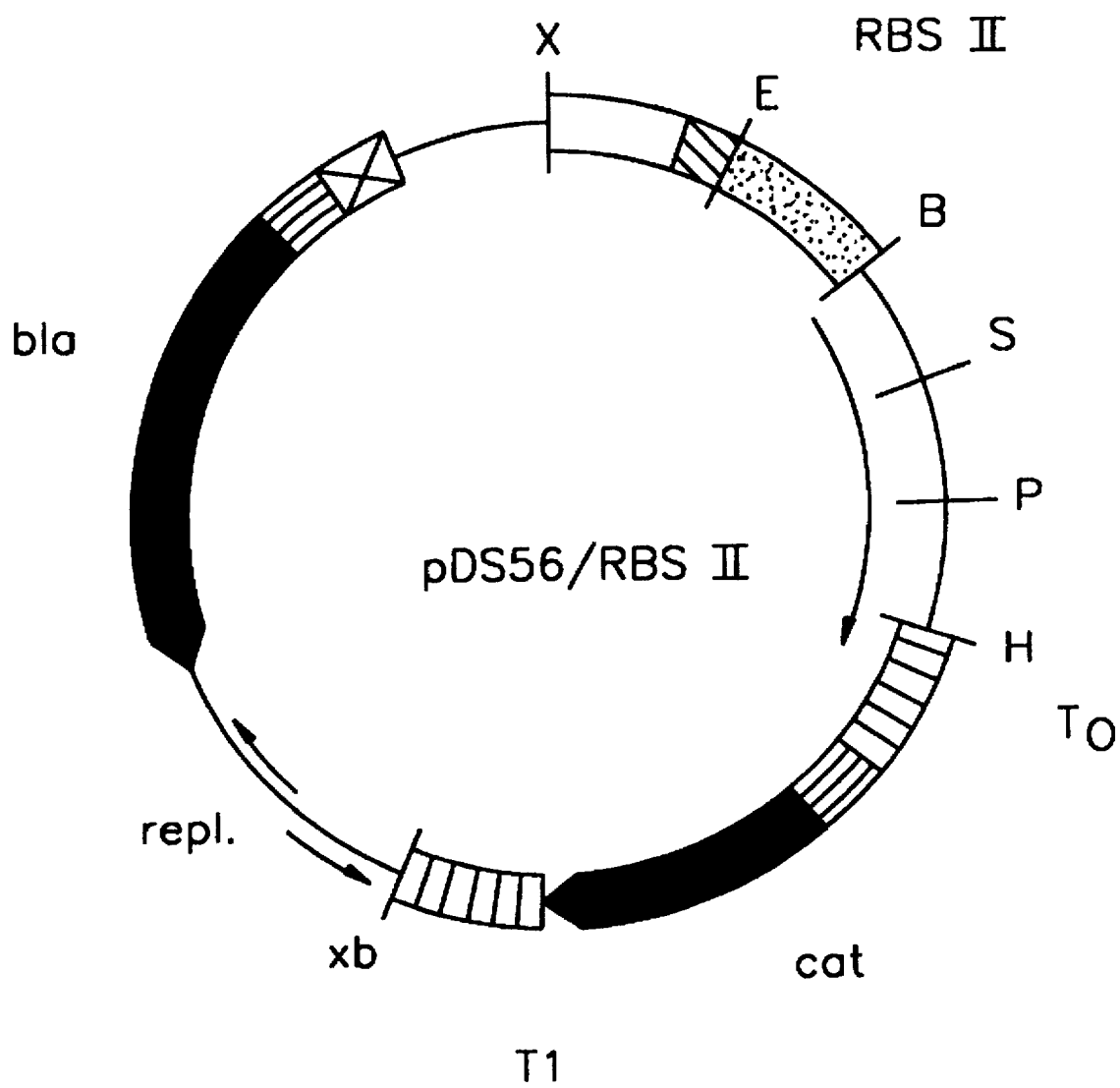

FIG. 11 Schematic representation of plasmid pDS56/RBSII.

FIG. 12A through FIG. 12C Nucleotide sequence of plasmid pDS56/RBSII. The cleavage sites for restriction enzymes set forth in FIG. 11 are overlined, while the region under control of the RBSII is underlined.

Figure 13:
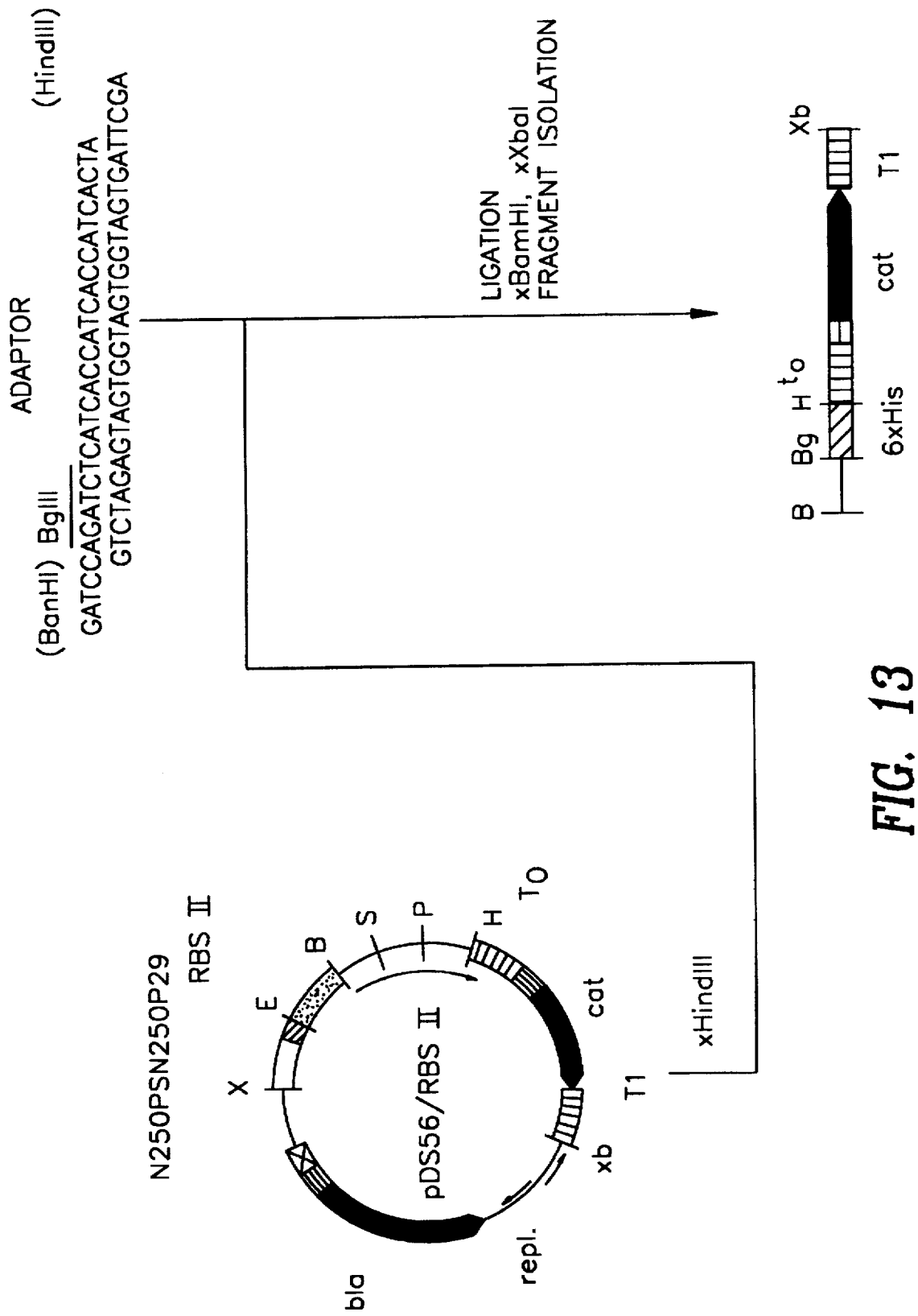

FIG. 13 Schematic representation of the construction and isolation of the BamHI/XbaI fragment containing the region coding for 6 histidines, the terminator $t_0$, the cat gene and the terminator T1, which was used in the construction of plasmid pRBSII-6xHis.

Figure 14:
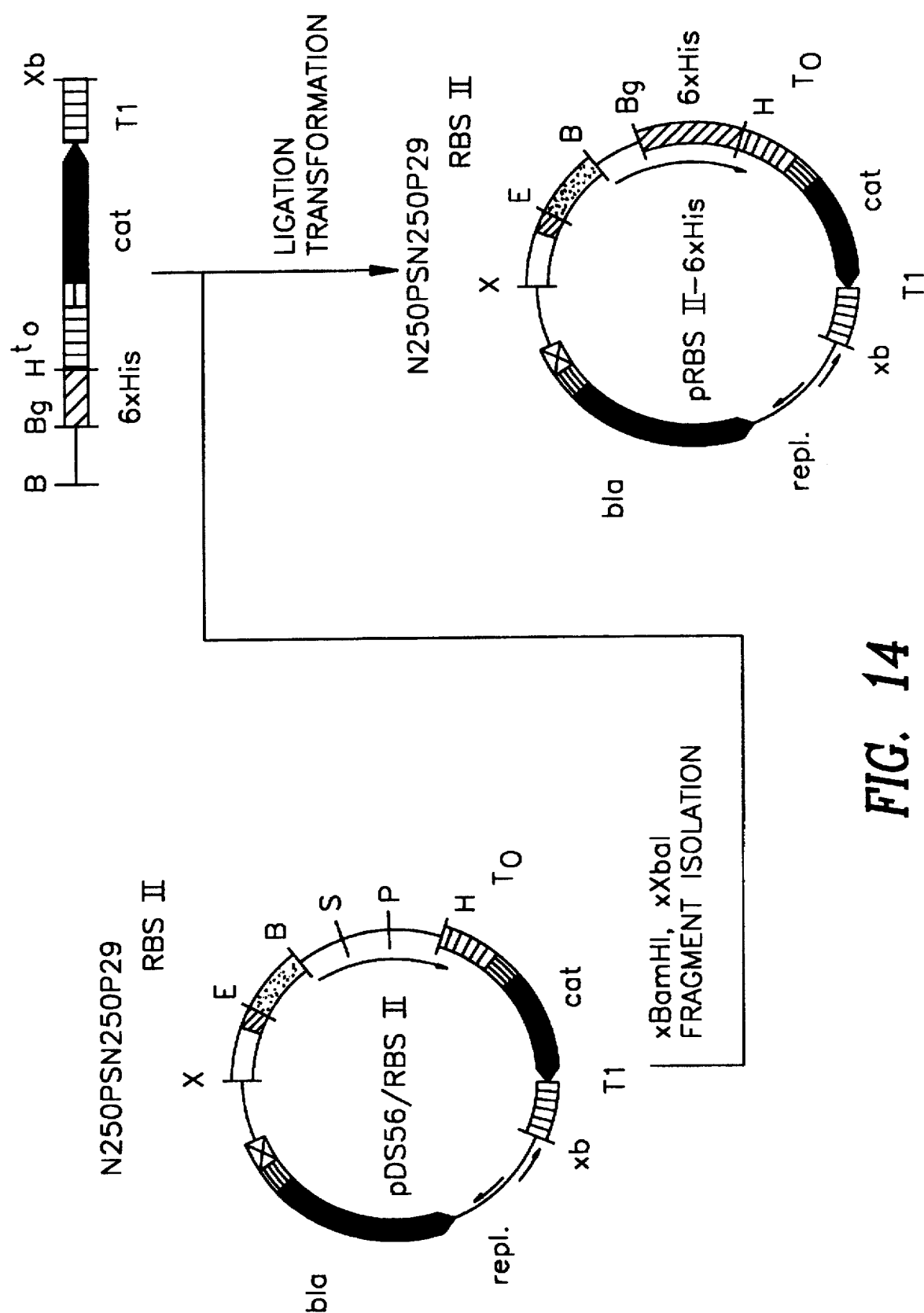

FIG. 14 Schematic representation of the construction of plasmid pRBSII-6xHis by linking the BamHI/XbaI fragment shown in FIG. 13 with the replication region-containing XbaI/BamHI fragment of plasmid pDS56/RBSII.

Figure 15:
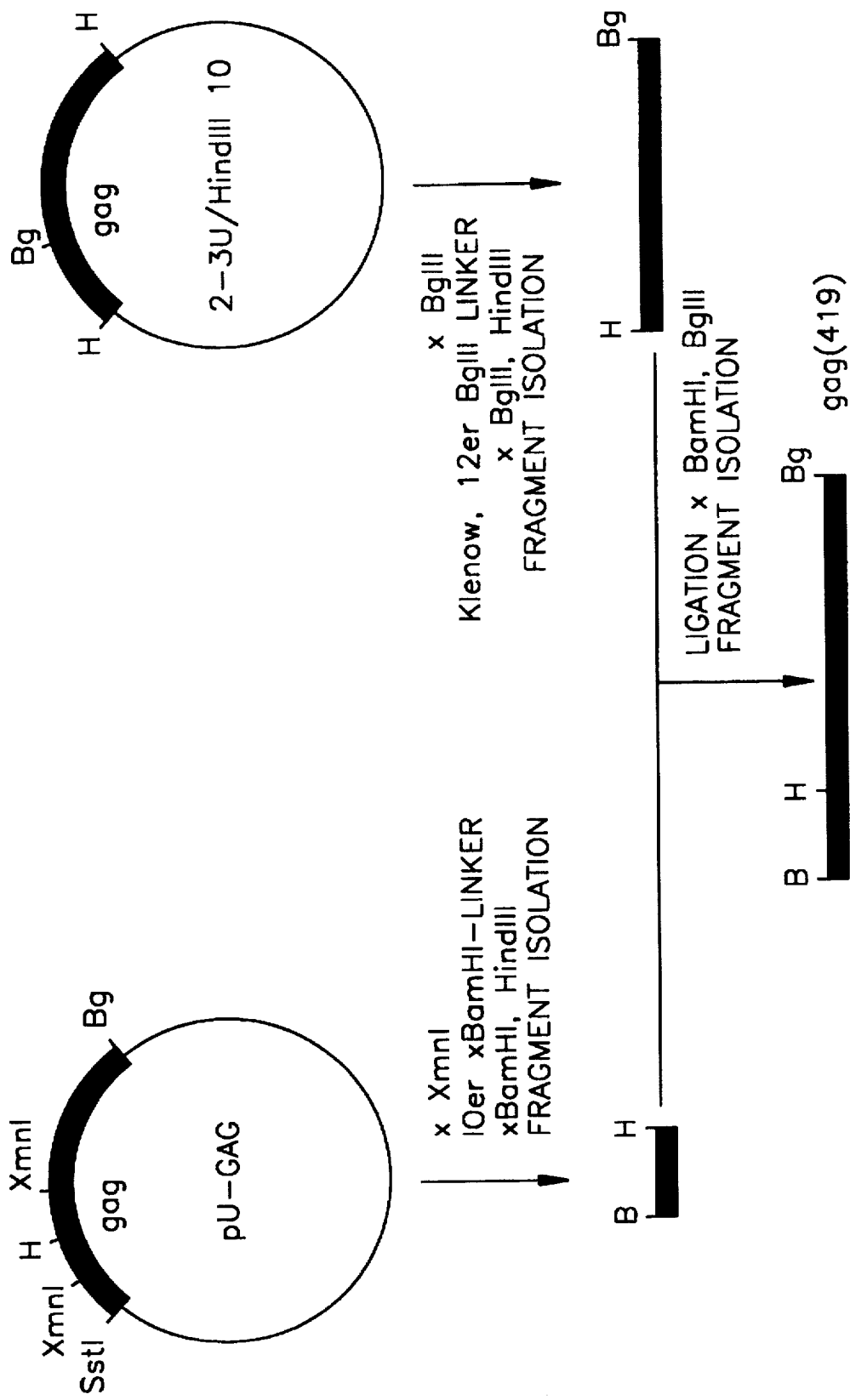

FIG. 15 Schematic representation of the production of the HIV-1 BamHI/BglII-gag(419) gene fragment.

FIG. 16 Representation of the nucleotide sequence of the HIV-1 gag gene fragment present in plasmid pU-GAG.

FIG. 17A through FIG. 17C Representation of the nucleotide sequence of the HIV-I gag gene fragment present in plasmid p2-3U/HindIII 10.

Figure 18:
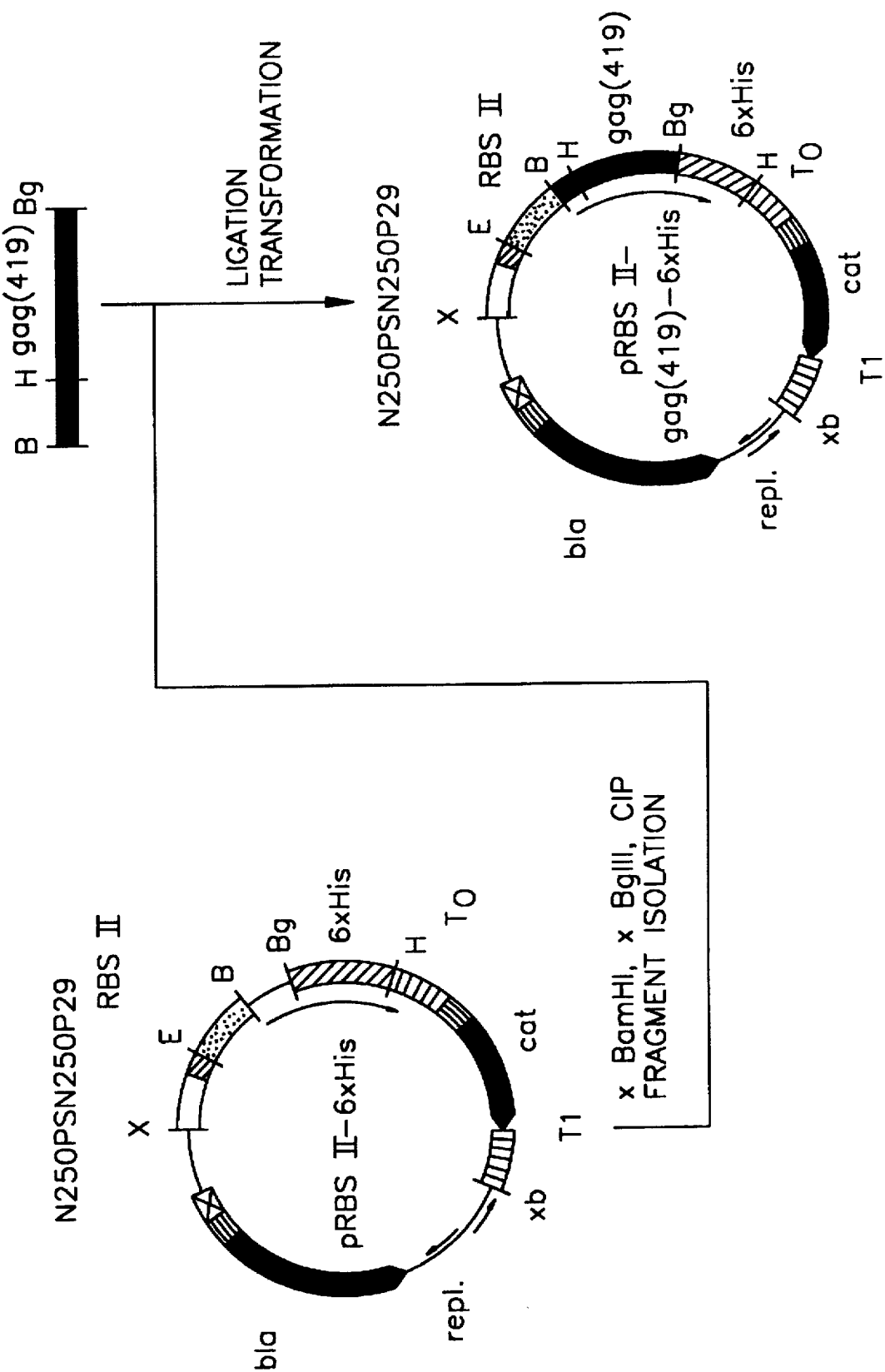

FIG. 18 Schematic representation of the construction of plasmid pRBSII-gag(419)-6xHis.

FIG. 19 Schematic representation of the construction of plasmid pRBSII-env(80)-gag(419)-6xHis.

Figure 20:
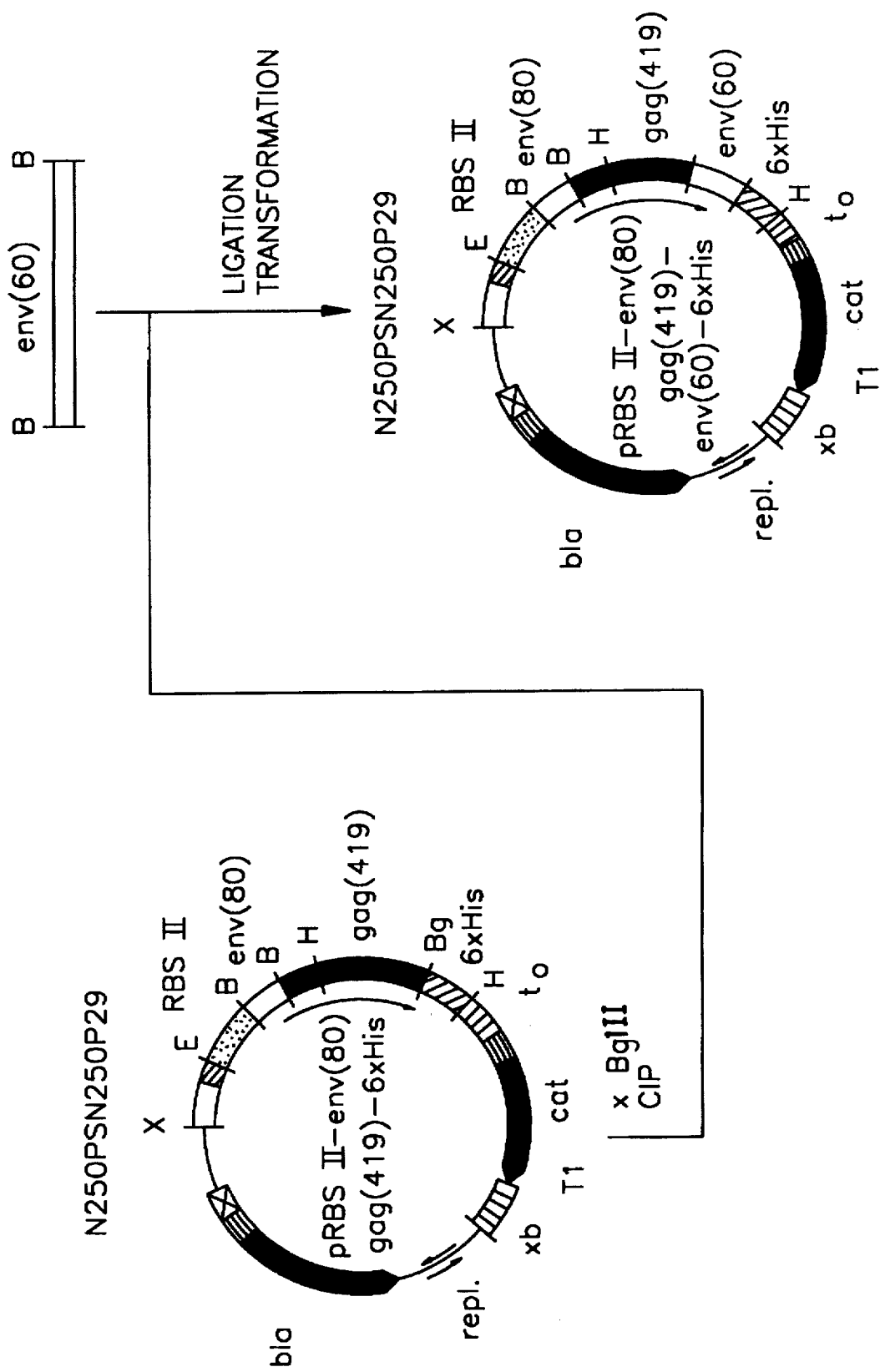

FIG. 20 Schematic representation of the construction of plasmid pRBSII-env(SO)-gag(419)-env(60)-6xHis.

DESCRIPTION OF THE INVENTION

The term "functional equivalent" which is used in connection with the polypeptides of the invention relates to polypeptides whose amino acid sequences have been derived from the amino acid sequences indicated above by nucleotide substitutions, deletions, insertions or additions and which correspond to at least one antigenic and/or immunogenic determinant of the HIV-2 env protein.

Certain substitutions in the amino acid sequence of a polypeptide have no influence on the biological activity of a polypeptide. Examples of such amino acid substitutions are Ala/Ser, Val/Ile, Asp/Glu, Thr/Ser, Ala/Gly, Ala/Thr, Set/ Ash, Ala/Val, Ser/Gly, Tyr/Phe, Ala/Pro, Lys/Arg, Asp/Asn, Leu/Ile, Leu/Val, Ala/Glu and vice versa (see Doolittle, in "The Proteins", ed. Neurath, H. and Hill, R. L., Academic Press, New York [1979]).

As used herein, the term "affinity peptide" means a peptide which contains an amino acid sequence which preferably binds to an affinity chromatographic carrier material. Examples of such affinity peptides are peptides which contain at least two adjacent histidine residues (see in this respect European Patent Application Publication No. 282 042). Such affinity peptides bind selectively to nitrilotriacetic acid-nickel chelate resins [Hochuli and Döbeli, Biol. Chem. Hoppe-Seyler 3.68, 748 (1987); European Patent Application Publication No. 253 303]. Polypeptides which contain such an affinity peptide can therefore be separated selectively from the remaining polypeptides. The affinity peptide can be linked either to the C-terminus or the N-terminus of the polypeptides having the amino acid sequence of formula I or subsequences or functional equivalents thereof.

The term "carrier polypeptide" which is used in connection with the polypeptides of the invention relates to such polypeptides which themselves contain no antigenic and/or immunogenic determinants of the HIV-2 env protein, but which are required for the expression of the polypeptides having the amino acid sequence of formula I or fragments or functional equivalents thereof. Preferred carrier polypeptides are E. coli chloramphenicol acetyltransferase (CAT) and mouse dihydrofolate reductase (DHFR).

Because of the process for their production, the polypeptides of the invention may contain methionine (coded for by ATG) as the first N-terminal amino acid. Alternatively, the microbial host may process the translation product partially or completely, whereby the N-terminal methionine is cleaved off.

The polypeptides of the invention can also be present in the form of multimers, e.g., in the form of dimers, trimers, tetramers etc. Of course, the polypeptides can also be covalently linked additionally with polypeptides whose amino acid sequence corresponds to at least one antigenic and/or immunogenic determinant of the HIV-2 core protein (gag).

The invention also provides DNA sequences which code for the polypeptides of the invention, recombinant vectors which contain these DNA sequences, single-cell organisms containing such vectors for the production of the polypeptides and processes for the production of such DNA sequences, recombinant vectors and single-cell organisms. Methods for the expression, isolation and purification of the polypeptides are also described. The thus-produced polypeptides can be used for a number of important immunological procedures, using the methods of this invention.

The polypeptides of the invention can be used as diagnostic reagents for the detection of antibodies against HIV-2 viruses in human sera or for the simultaneous detection of antibodies against HIV-1 and HIV-2 viruses (referred to hereinafter collectively as antibodies against HIV viruses) in human sera. Since they can be produced in homogeneous form, problems with nonspecific reactions, which in the past have limited the use of diagnostic reagents based on relatively crude viral HIV protein lysates, can be eliminated.

When used as an immunogen, the polypeptides of the invention can be used in animals to produce antibodies which are directed against the antigenic determinants contained in these polypeptides. Such antibodies can be used, in turn, in combination with the polypeptides, which have been appropriately labelled, in a radioimmunoassay (RIA) or in an enzyme immunoassay (ELISA) to detect the presence of HIV-2 viruses or HIV-1 and HIV-2 viruses (referred to hereinafter collectively as HIV viruses) or particles thereof in human sera or in other biological fluids such as, e.g., in tears, semen, vaginal secretions and saliva. The particles (or fragments) of HIV viruses which can be detected using these methods include, of course, pieces of the vital HIV envelope proteins (env).

The polypeptides of the invention can be produced using conventional methods of peptide synthesis in the liquid phase or, preferably, on the solid phase, such as the methods of Merrifield (J. Am. Chem. Soc. 85, 2149–2154 [1963]), or by other equivalent methods known in the art.

Alternatively, the polypeptides can be produced using methods of DNA recombinant technology [Maniatis et al. in "Molecular Cloning - A Laboratory Manual", Cold Spring Harbor Laboratory (1982), hereby incorporated by reference]. For example, the DNA sequences which code for the polypeptides of the invention can be, synthesized by conventional chemical methods, e.g., by the phosphotriester method [Narang et al., in Meth. Enzymol. 68, 90–108 (1979)] or by the phosphodiester method [Brown et al., Meth. Enzymol. 68, 109–151 (1979)]. In both methods long oligonucleotides are usually synthesized which are joined to one another in the aforementioned manner. The nucleotide sequences of the DNA fragments can be identical with those nucleotide sequences which code for the natural HIV-2 or HIV-1 and HIV-2 polypeptides. Since the genetic code is degenerate, however, it will be understood that partially or completely different nucleotide sequences can also code for the same polypeptides. If desired, there can be selected for the nucleotide sequences those codons which are also preferably used by the host organism for the expression of the polypeptide [Grosjean et al., Gene 18, 199–209 (1982)]. Care must be taken, however, to ensure that the thus-obtained DNA sequences do not contain partial sequences which make the construction of the expression vectors difficult, e.g., by introducing an undesired restriction enzyme cleavage site.

The DNA sequences which code for the polypeptides of the invention can also be produced by isolating a DNA fragment which codes for the amino acid sequence of formula I from isolated proviral HIV-2 DNA or from genomic DNA of cells in which the proviral HIV-2 genome has been integrated, and subsequently incorporating the fragment into a suitable vector which codes for the partial sequences A and C of the general formulae A-B-C, A-C-B and C-B-A.

After the production of the DNA sequences which code for the polypeptides of the invention, the sequences can be incorporated using known methods into any suitable expression vector which produces the requisite expression signals. Suitable vectors can be constructed from segments of chromosomal, non-chromosomal and synthetic DNA sequences such as, e.g., various known plasmids and phage DNA's. Examples of such vectors can be found in the aforementioned textbook of Maniatis et al. Especially suitable vectors are plasmids of the pDS family [Bujard et al., Methods in Enzymology, eds. Wu and Grossmann, Academic Press, Inc., Vol. 155, 416–433 (1987)].

In the preferred embodiment of the present invention, a synthetic BamH1 fragment which codes for the amino acid sequence of formula I (env(60) gene) was fused with BamH1 or BglII-cleaved DNA of plasmid pDS78/RBSII, 6xHis and with BglII-cleaved DNA of plasmid pRBSII-env (80)-gag(419)-6xHis, to isolate the expression vectors penv (60)-DHFR, pDHFR-env(60) and pRBSII-env(80)-gag (419)-env(60)-6xHis which code for the synthesis of the especially preferred polypeptides of formulae II–IV of the invention. The synthesis of the synthetic env(60) gene is described in Example 1. Its nucleotide sequence and the amino acid sequence (ENV(60)) derived therefrom are shown in FIG. 1. The constructions of plasmids pDS78/ RBSII,6xHis, penv(60)-DHFR, pDHFR-env(60), pRBSII-env(80)-gag(419)-6xHis and pRBSII-env(80)-gag(419)-env (60)-6xHis are described in detail in Examples 2-4, 6 and 7.

Expression vectors which contain the DNA sequences coding for the polypeptides of the invention operatively linked with an expression control sequence can be incorporated using conventional methods into any suitable host organism. The selection of a suitable host organism is determined by different factors which are well known in the art. Thus, for example, compatibility with the chosen vector, toxicity of the expression product, expression characteristics, necessary biological safety precautions and costs play a role and a compromise between all of these factors must be found.

Suitable host organisms include gram-negative and gram-positive bacteria, for example *E. coli* and *B. subtilis* strains. Especially preferred host organism of the present invention are *E. coli* strain M15 (described as OZ 291 by Villarejo et al. in J. Bacteriol. 120, 466–474 [1974]) and *E. coli* W3110 (ATCC No. 27325). In addition to the aforementioned *E. coli* strain, however, other generally accessible *E. coli* strains such as *E. coli* 294 (ATCC No. 31446) and *E. coli* RR1 (ATCC No. 31343) can also be used.

The manner in which the expression of the polypeptides of the invention is carried out depends on the chosen expression vector/host cell system. Usually, the host organisms which contain a desired expression vector are grown under conditions which are optimal for the growth of the host organisms. At the end of the exponential growth, when the increase in cell number per unit time decreases, the expression of the desired polypeptide is induced, i.e. the DNA coding for the desired polypeptide is transcribed and the transcribed mRNA is translated. The induction can be carried out by adding an inducer or a derepressor to the growth medium or by altering a physical parameter, e.g., a change in temperature. In the expression vectors used in the preferred embodiments of the present invention, the expression is controlled by the lac repressor. By adding isopropyl-β-D-thiogalactopyranoside (IPTG), the expression control sequence is derepressed and the synthesis of the desired polypeptide is thereby induced.

For the isolation of small amounts of the polypeptides of the invention for analytical purposes, e.g., for polyacrylamide gel electrophoreies, the host organisms can be disrupted by treatment with a detergent, e.g., sodium dodecyl sulphate (SDS). Larger quantities of the polypeptides can be recovered by mechanical [Charm et al., Meth, Enzymol. 22, 476–556 (1971)], enzymatic (lysozyme treatment) or chemical (detergent treatment, urea or guanidinium chloride treatment, etc.) means or by a combination of these means.

After the polypeptides of the invention have been removed from the host organisms they can be purified by known methods, e.g., by centrifugation at different velocities, precipitation with ammonium sulphate, dialysis (at normal pressure or at reduced pressure), preparative isoelectric focusing, preparative gel electrophoresis or by various chromatographic methods such as gel filtration, high performance liquid chromatography (HPLC), ion exchange chromatography, reverse phase chromatography and affinity chromatography (e.g., on Sepharose® Blue Cl-6B or on carrier-bound monoclonal antibodies which are directed against the polypeptides of the invention). Preferably, the polypeptides of the invention are purified on nitrilotriacetic acid (NTA) resins of the general formula Carrier matrix-Spacer-NH-$(CH_2)_x$—$CH(COOH$—$N(CH_2COO^-)_2Ni^{2+}$ in which x signifies 2, 3 or 4. Suitable carrier matricies include materials which are used in affinity and gel chromatography, for example cross-linked dextrans, agarose (especially in the form known under the trademark Sepharose®) or polyacrylamides. Useful spacers include the spacer groups which are well known in affinity chromatography, with the groups —O—$CH_2$—$CH(OH)$—$CH_2$— and —O—CO— being preferred.

An especially preferred NTA resin for the purification of the polypeptides has the formula [Sepharose®CL 6B]—O—$CH_2$—$CH(OH)$—$CH_2$—$NH$—$(CH_2)_4CH(COOH)$—N$(CH_2COO^-)_2$ $Ni^{2+}$.

As mentioned previously, the polypeptides of the invention which are obtainable using the previously described methods can be used as a diagnostic tool for the detection of antibodies against HIV viruses in human sera. To this end, the polypeptides of the invention can be used in numerous, known detection methods.

For example, the polypeptides can be labelled using known methods and these labelled polypeptides can then be added to a human serum sample suspected to contain antibodies against HIV viruses to form labelled polypeptide/ antibody complexes. The complexes thus formed can then be detected using conventional methods.

The polypeptides of the invention can also first be immobilized on a solid support and then brought into contact with a human serum sample. Antibodies against HIV viruses in the sample bind to this immobilized polypeptide and, after removing non-bond polypeptides and antibodies by washing, the thus-formed complexes can be detected using a reagent such as *Staphylococcus aureus* protein A (labelled, for example, with $^{125}$iodine) or a second anti-Ig antibody (labelled, for example, with a radioisotope or with horseradish peroxidase). Many modifications and variations of these detection methods will be apparent to the person skilled in the art, of which some are suggested hereinafter.

Different diagnostic tests for the detection of HIV viruses or fragments thereof in human sera or in other biological fluids can be developed by using antibodies against the polypeptides of the invention (hereinafter anti-HIV antibodies). Such antibodies can be produced by injecting an immunogenic composition containing a polypeptide of the invention and a physiologically compatible carrier material into a mammal or bird. The amount of protein required for the injection is known to the person skilled in the art or can be determined by routine experimentation using known methods. The term "carrier material" used in connection with the present invention relates either to known compositions which are suitable for administration to human beings or to known adjuvants which are used in the inoculation of animals.

Suitable adjuvants for use in human beings and animals are well known in the art [WHO Techn. Rep. Series 595, 1–400 (1976); Jollis et al., "Chemical and Biological Basis of Adjuvants", in Molecular Biochemistry and Biophysics Vol. 13, 1–148 (1973) Springer Verlag Berlin]. The polypeptides of the invention can also be administered after incorporation in liposomes or other micro-carrier materials, or after coupling to polysaccharides, other polypeptides or other polymers.

One or more additional inoculations (boosters) are generally administered a few weeks after the first inoculation, to produce a high titer of anti-HIV antibodies. These can then be isolated using standard methods.

Of course, monoclonal antibodies can also be used for the aforementioned tests. The methods for the production of such antibodies are well known in the art [Köhler et al., Nature 256, 495–497 (1975)].

As explained previously, the anti-HIV antibodies can be used in various diagnostic tests for the detection of HIV viruses or fragments thereof. Such tests can be carried out in the form of radioimmunoassays, either in solution or on a solid support. However, enzyme immunoassays can also be carried out. The tests can be carried out either directly or indirectly by means of a second antibody which is directed against the anti-HIV antibody. Numerous enzyme activities can be coupled to the anti-bodies, e.g., peroxidase, glucose oxidase, β-galactosidase and alkaline phosphatase, which produce a coloration after the addition of a substrate solution.

The principle underlying many of these tests is that human serum or other biological fluids suspected to contain HIV viruses or fragments thereof is/are reacted with a known titer of anti-HIV antibodies to form antigan/antibody complexes. The complexes thus formed are detected using conventional methods.

It will be evident to those skilled in the art that many other detection methods employing the anti-HIV antisera can also be used, such as various agglutination tests. In agglutination tests, the interaction between antibodies and HIV viruses or fragments thereof is detected using particles coated with anti-HIV antibodies. Such particles are, for example, latex beads, liposomes, erythrocytes, polyacrylamide beads or any of a number of suitable polymers.

The previously described methods for the detection of HIV viruses or antibodies against HIV viruses can be carried out using suitable test kits consisting of a container which contains a polypeptide of the invention or anti-HIV antibodies of the present invention.

EXAMPLES

The following, nonlimiting examples will further serve to illustrate this invention. Unless otherwise specified, percentages given below for solids in solid mixtures, liquids in liquids and solids in liquids are on a wt/wt, vol/vol and wt/vol basis, respectively.

Example 1

Production of the Synthetic HIV-2 Env(60) Gene
A) Principles

The synthetic HIV-2 env(60) gene was constructed from 14 oligonucleotide fragments, the length of which varied between 17 and 31 nucleotides (see FIG. 1).
B) Synthesis of the Oligonucleotide Fragments The oligonucleotide fragments 1–14 were synthesized simultaneously on solid carrier material using the procedure described by Bannwarth and Iaiza in DNA 5, 413–419 (1986).

C) Combination of the Oligonucleotide Fragments 100 pmol of each of the oligonucleotide fragments 2, 3, 8, 9, 10 and, respectively, 4, 5, 6, 7, 11, 12, 13 were phosphorylated at 37° C. for 15 minutes in 100 μl of kinase buffer [Maniatis et al., "Molecular Cloning", Cold Spring Harbor Laboratory (1982)] containing 100 units of polynucleotide kinase and 100 μCi of γ-$^{32}$P-ATP (5000 Ci/mmol). Thereafter, a 10-fold excess of cold ATP was added to the reaction mixtures. After a further incubation period of 90 minutes, the polynucleotide kinase was heat-inactivated (2 minutes. 95° C.) and, after the addition of 10 μl of 5M lithium acetate (LiOAc) and 100 μl of isopropanol, the phosphorylated oligonucleotide fragments were precipitated for 30 minutes at −78° C. The precipitated oligonucleotide fragments were then washed with ethanol and dried.

The phosphorylated oligonucleotide fragments 2, 3, 8, 9, 10 and the non-phosphorylated fragment 1 and, respectively, the phosphorylated oligonucleotide fragments 4, 5, 6, 7, 11, 12, 13 and the non-phosphorylated fragment 14 were hybridized according to known methods described in the literature [Maniatis et al., supra] and then ligated (37° C., 1.5 hours) in 100 μl of ligase buffer [Maniatis et al., supra] containing 31 units of T4 ligase. Subsequently, the two sub-fragments obtained were precipitated as previously described, then washed with ethanol and dried.

The two sub-fragments were subsequently separated by 6% polyacrylamide gel electrophoresis, eluted according standard methods [Maniatis et al., supra], freed from salts by using a Sephadex G-50 column and linked with one another by using T4 ligase as previously described, to give the desired HIV-2 env(60) gene. After purification of the HIV-2 env(60) gene by the previously described procedure (polyacrylamide gel electrophoresis, elution and removal of salts), the gene was phosphorylated as previously described.

Example 2

Construction of Plasmid pDS78/RBSII,6xHis
A. Description of Plasmids pDS78/RBSII and pDMI,1

For the construction of plasmid pDS78/RBSII,6xHis plasmid pDS78/RBSII was chosen. E. coli cells transformed with this plasmid and with plasmid pDMI,1 have been deposited under the Budapest Treaty at the Deutschen Sammlung Yon Mikroorganismen in Göttingen on the Sep. 3, 1987 [E. coli M15 (pDS78/RBSII, pDMI.1), DSM No. 4232].

The part of pDS78/RBSII (FIGS. 2 and 3) which lies between the restriction cleavage sites for XbaI and XhoI and which contains the replication region and the gene for β-lactamase, which confers ampicillin resistance to the cells, was derived originally from the plasmid pBR322 [Bolivar et al., Gene 2, 95–113 (1977); Sutcliffe, Cold Spring Harbor Symp. Quant. Biol. 43, 77–90 (1979)]. However, the gene for β-lactamase was modified so that the cleavage sites for the restriction enzymes HincII and PstI were eliminated. These alterations in the DNA sequence did not, however, affect the amino acid sequence of the β-lactamase.

The remaining part of the plasmid carries the regulatable promoter/operator element N25OPSN25OP29 and the ribosomal binding site RBSII. This ribosomal binding site was derived from the ribosomal binding site of the promoter $P_{G25}$ of the E. coli phage T5 [R. Gentz, Thesis, University of Heidelberg, BED (1984)] and was obtained as an EcoRI/BamHI fragment by DNA synthesis. This is followed by the dihydrofolate reductase gene of the mouse cell line AT-3000 [Chang et al., Nature 275, 617–624 (1978); Masters et al., Gene 21, 59–63 (1983)], which was altered by introducing a cleavage site for the restriction enzyme BglII directly in front of the termination codon for translation.

Plasmid pDS78/RBSII also contains the terminator $t_o$ of the *E. coli* phage lambda [Schwarz et al., Nature 272, 410–414 (1978)], the promoter-free gene of chloramphenicol acetyltransferase [Marcoli et al., FEBS Letters, 110, 11–14 (1980)] and the terminator T1 of the *E. coli* rrnB operon [Brosius et al., J. Mol. Biol., 148, 107–127 (1981)].

Plasmid pDS78/RBSII contains the regularable promoter/operator element N25OPSN25OP29 and the ribosomal binding site RBSII. Because of the high efficiency of this expression signal, plasmid pDS78/RBSII and derivatives thereof such as plasmid pDS78/RBSII,6xHis can be stably maintained in *E. coli* cells only when the promoter/operator element is repressed by the binding of a lac repressor to the operator. The lac repressor is coded by the lacI gene. N25OPSN25OP29 can be repressed efficiently only when a sufficient number of repressor molecules are present in the cells. Therefore, the lacI$^q$ allele, which contains a promoter mutant that produces an increased expression of the repressor gene, was used.

This lacI$^q$ allele is contained in the plasmid pDMI,1 (FIGS. 4 and 5). This plasmid carries, in addition to the lacI gene, the neogene which confers kanamycin resistance to the bacteria and which is used as a selection marker. pDMI,1 is compatible with the above-mentioned plasmids. *E. coli* cells which are transformed with such expression vectors must contain pDMI,1 to guarantee that the expression vector is maintained stable in the cells. Induction of this system is achieved by adding IPTG to the medium at the desired cell density.

Plasmid pDMI,1 (FIGS. 4 and 5) carries the neo gene of neomycin phosphotransferase from the transposon Tn5 [Beck et al., Gene 19, 327–336 (1982)], which confers kanamycin resistance to the *E. coli* cells, and the lacI gene [Farabough, Nature 274, 765–769 (1978)] having the promoter mutation I$^q$ [Calos, Nature 274, 762–765 (1978)], which codes for the lac repressor. Moreover, the plasmid pDMI,1 contains a region of plasmid pACYC184 [Chang et al. J. Bacteriol. 134, 1141–1156 (1978)] which contains all of the information required for replication and stable transmission to the daughter cells.

B. Construction of Plasmid pDS78/RBSII,6xHis

For the construction of plasmid pDS78/RBSII,6xHis (FIGS. 6 and 7), the EcoRI/BamHI fragment of plasmid pDS78/RBSII comprising the ribosomal binding site RBSII was combined with a region coding for six histidines.

For this purpose, two complementary oligo-nucleotides, the nucleotide sequences of which are represented in FIG. 6 as a double-stranded DNA sequence, were synthesized as previously described (Ex. 1, section B). The lyophilized oligonucleotides were taken up in water and dissolved at 4° C. for 1 hour. The DNA concentration was 100 nmol/ml.

For the phosphorylation, 150 pmol of each of the two oligonucleotides in 20 µl of 50 mM Tris/HCl [pH 8.5] and 10 mM MgCl$_2$ were incubated at 37° C. for 20 minutes with 2 pmol of $\gamma$-[$^{32}$P]-ATP (5000 Ci/mmol) and 1 unit (U) of T4-polynucleotide kinase. Subsequently, 5 nmol of ATP were added and, after a further 20 minutes at 37° C., the reactions were terminated by heating to 65° C.

The DNA of the plasmid pDS78/RBSII was prepared for ligation with the two phosphorylated oligonucleotides by first cleaving 2 pmol of the plasmid DNA with the restriction enzyme BamHI. The DNA was extracted with phenol, washed with ether and then precipitated using, lithium acetate/isopropanol as previously described. The sediment was dried and taken up in 20 µl of TE buffer.

For the ligation with the phosphorylated oligonucleotides, 1.5 pmol of the plasmid DNA cleaved with BaHII were incubated at 15° C. for 2 hours with 60 pmol of each of the phosphorylated oligonucleotides in ligase buffer containing 2 units of T4-DNA ligase. After an incubation at 65° C. for 5 minutes, the ligated DNA was cleaved with the restriction enzymes XhoI and BamHI. Thereafter, the XhoI/Bam/4I fragment containing the regulatable promoter N25OPSN25OP29, the ribosomal binding site RBSII and the region coding for 6 histidines (FIG. 6) was isolated by agarose gel electrophoresis.

For the construction of plasmid pDS78/RBSII,6xHis, the above XhoI/BamHI fragment was integrated into plasmid pDS78/RBSII, whereby the original XhoI/BamHI fragment of this plasmid was replaced (FIG. 7). For this purpose, 1 pmol of DNA of plasmid pDS78/RBSII was cleaved with the restriction enzymes XhoI and BamHI, before the larger DNA fragment was isolated by agarose gel electrophoresis. 0.05 pmol of this fragment were then incubated at 15° C. for 2 hours with 0.1 pmol of the isolated XhoI/BamHI fragment in ligation buffer containing 2 units of T4-DNA ligase.

*E. coli* M15 cells containing plasmid pDMI,1 were prepared for the transformation by the method of Morrison [Methods Enzymol. 68, 326–331 (1979)]. After heating to 65° C. for 7 minutes the ligation mixture was added to 200 µl of these competent cells. The sample was held in ice for 30 minutes, incubated at 42° C. for 2 minutes and, after the addition of 0.5 ml of LB medium, incubated at 37° C. for 90 minutes.

The transformed cells were then plated onto LB agar plates containing 100 µg/ml ampicillin and 25 µl/ml kanamycin, and the plates were incubated at 37° C. overnight. Individual colonies were picked with a sterile toothpick, transferred into a test tube which contained 10 ml LB medium containing 100 µl/ml ampicillin and 25 µg/ml kanamycin and incubated for 12 hours in a shaking incubator. Thereafter, the cells were sedimented and the plasmid DNA was isolated using the method of Birnboim and Doly [Nucleic Acids Res. 7, 1515–1523 (1979)].

0.2 µg of each of the isolated plasmids were cleaved with the restriction enzymes XhoI and BamHI to determine whether a fragment which contains the regulatable operator/repressor element N25OPSN25OP29, the ribosomal binding site RBSII and the region coding for the six histidines was present in these plasmids. Plasmids containing such a fragment were designed pDS78/RBSII,6xHis (FIG. 7).

To demonstrate that the correct sequence was present in pDS78/RBSII,6xHis, the double-stranded circular plasmid DNA was sequenced, using a $\gamma$-[$^{32}$P]-ATP labelled starter sequence (primer). This starter sequence contained the nucleotides of position 89–108 of plasmid pDS78/RBSII. 0.3 pmol of the isolated plasmid DNA were precipitated with alcohol, the sediment was washed once with 80% ethanol, dried and finally dissolved in 8 µl of ¼ TE buffer. The sample was incubated at 95° C. for 5 minutes, cooled to 0° C. and centrifuged (Eppendorf bench centrifuge, 2 minutes, 12,000 rpm). 1.5 pmol of the starter sequence in a volume of 2 µl were added before the sample was incubated first at 95° C. for 2 minutes and then at 42° C. for 5 minutes. The DNA was sequenced using the method of Sanger et al. [Proc. Natl. Acad. Sci. USA 74, 5463–6567 (1977)]. Because a radioactively labelled "primer" was used, all reactions were carried out with unlabelled deoxynucleotide triphosphates. The DNA sequence analysis indicated that pDS78/RBSII, 6xHis contained the sequence given in FIG. 6.

Example 3

Construction of Plasmid penv(60)-DHFR

A) Principles

For the construction of plasmid penv(60)-DHFR, plasmid pDS78/RBSII,6xHis linearized with the restriction enzyme BamHI was linked with the synthetically produced env(60) gene (FIG. 8).

B) Preparation of Plasmid pDS78/RBSII,6xHis Linearized with BamHI (Fragment 1)

4 pmol of plasmid pDS78/RBSII were cleaved with the restriction enzyme BamHI. Subsequently, the DNA was treated with CIP [calf intestinal phosphatase]. The enzymes were then heat-inactivated and, after the addition of sample buffer, the DNA was separated in a 1% low melt agarose gel. After staining with ethidium bromide, the corresponding DNA band was cut out under UV light (300 nm) and the DNA was extracted using standard methods [Maniatis et al., supra ].

C) Preparation of the HIV-2 Env(60) Gene (Fragment 2)

The preparation of this gene is described in Example 1.

D) Production of Plasmid penv(60)-DHFR 0.05 pmol of Fragment 1 and 0.1 pmol of Fragment 2 were incubated (15° C. 2 hours) with 1U of T4 ligase. After heat inactivation of the enzyme, the DNA was transformed into the E. coli strain M15 containing plasmid pDMI,1. The cells were plated onto LB agar plates containing 100 µg/ml ampicillin and 25 µg/ml kanamycin. The plates were incubated at 37° C. for 15 hours. The ligation gave about 500 colonies. Individual colonies were each transferred into 10 ml of LB medium and grown at 37° C. overnight, and their plasmid DNAs were subsequently isolated using standard methods [Maniatis et al., supra].

E) Sequence Analysis of the HIV-2 Env(60) Gene Integrated into Plasmid pDS78/RBSII,6xHis To demonstrate that the Correct HIV-2 env(60) gene sequence was present in the correct orientation in the BamHI site of plasmid pDS78/RBSII,6xHis, the double-stranded circular plasmid DNA was sequenced, using a starter sequence (primer) labelled with [$\gamma$-$^{32}$P]-ATP.

0.3 pmol of the isolated plasmid DNA were precipitated with alcohol, the sediment was washed once with 80% ethanol, dried and finally dissolved in 8 µl of ¼ TE buffer. After the addition of 2 pmol of the radioactively labelled starter sequence, the sample was incubated first at 95° C. for 2 minutes and then at 42° for 5 minutes. The DNA was then sequenced by the method of Sanger et al. [Proc. Natl. Acad. Sci. USA 74, 5463–6567 (1977)]. The sequence analysis indicated that the correct HIV-2 env(60) gene sequence had been integrated into the BamHI restriction site of plasmid pDS78/RBSII,6xHis.

Example 4

Construction of Plasmid pDHFR-env(60)

A) Principles

For the construction of plasmid pDHFR-env(60), plasmid pDS78/RBSII,6xHis linearized with the restriction enzyme BglII was linked with the synthetically produced env(60) gene (FIG. 9).

B) Preparation of BqlII-linearized Plasmid pDS78/RBSII, 6xHis (Fragment 1)

4 pmol of plasmid pDS78/RBSII,6xHis were cleaved with the restriction enzyme BglII. Subsequently, the DNA was treated with CIP. The enzymes were then heat-inactivated and, after the addition of sample buffer, the DNA was separated in a 1% low melt agarose gel. After staining with ethidium bromide, the corresponding DNA band was cut out under UV light (300 nm) and the DNA was extracted using standard methods [Maniatis et al., supra].

C) Preparation of the HIV-2 Env(60) Gene (Fragment

The preparation of this gene is described in Example 1.

D) Production of Plasmid pDHFR-env(60)

0.05 pmol of Fragment 1 and 0.1 pmol of Fragment 2 were incubated (15° C., 2 hours) with 1U of T4 ligase. After heat inactivation of the enzyme, the DNA was transformed into E. coli strain M15 which contained the plasmid pDML1. The cells were platen onto LB agar plates containing 100 µg/ml ampicillin and 25 µg/ml kanamycin. The plates were incubated at 37° C. for 15 hours. The ligation gave about 500 colonies. Individual colonies were grown at 37° C. overnight in 10 ml of LB medium and their plasmid DNAs were subsequently isolated using standard methods [Maniatis et al., supra].

E) Sequence Analysis of the HIV-2 Env(60) Gene Integrated into Plasmid pDS78/RBSII,6xHis To demonstrate that the correct HIV-2 env(60) gene sequence was present in the correct orientation in the BglII site of plasmid pDS78/RBSII,6xHis, the double-stranded circular plasmid DNA was sequenced, using a starter sequence (primer) labelled with [$\gamma$-$^{32}$P]-ATP.

0.3 pmol of the isolated plasmid DNA was precipitated with alcohol, the sediment was washed once with 80% ethanol, dried and finally dissolved in 8 µl of ¼ TE buffer. After the addition of 2 pmol of the radioactively labelled primer, the sample was incubated first at 95° C. for 2 minutes and then at 42° for 5 minutes. The DNA was then sequenced by the method of Sanger et al. [Proc. Natl. Acad. Sci. USA 74, 5463–6567 (1977)]. The sequence analysis indicated that the correct HIV-2 env(60) gene sequence had been integrated into the BglII restriction site of plasmid pDS78/RBSII,6xHis.

Example 5

Reactivity of the ENV(60)-DHFR and DHFR-ENV(60) Polypeptides with HIV-positive Sera.

A. Principles

To demonstrate that the env(60) gene codes for an antigenic determinant which is recognized by antibodies in sera of persons infected with HIV-2, the polypeptides ENV(60)-DHFR and DHFR-ENV(60) were expressed in E. coli, transferred to a nitrocellulose filter and incubated with suitable sera. The HIV-1 ENV(80)-DHFR polypeptide [Certa et al., EMBO J. 5, 3051–3056 (1986)] was used as the control.

B. Expression of the ENV(60)-DHFR and DHFR-ENV(60) Polypeptides in E. coli

E. coliM15 cells containing plasmid pDMI,1 were transformed with plasmid penv(60)-DHFR or pDHFR-env(60) and grown in LB medium [Maniatis et al., supra] containing 100 µg/ml ampicillin and 20 µg/ml kanamycin. The cultures were induced with IPTG (2 mM final conc.) at an optical density of OD$_{600}$=0.7 and grown for 4 hours. Thereafter, the cells were harvested by centrifugation.

C. Analysis of the ENV(60)-DHFR and DHFR-ENV(60) Polypeptides Expressed in E. coli 50 µl of the cell cultures were re-suspended in 125 mM Tris-HCl, pH 6.8, containing 3% SDS, 3% β-mercaptoethanol and 20% glycerol. The samples were boiled for 5 minutes and subsequently separated using 12.5% polyacrylamide gel electrophoresis [U.K. Laemmli, Nature 227, 680–685 (1970)]. The protein bands were visualized using Coomassie blue staining (FIG. 10, upper part).

D. Reactivity of the ENV(60)-DHFR and DHFR-ENV(60) Polypeptides with HIV Antibodies Probes of the induced cell cultures (see section B), an E. coli control lysate and purified HIV-1 ENV(80)-DHFR polypeptide (1 μg per lane) were separated electrophoretically (2 gels) as described in paragraph C. Each of the unstained gels was covered with a nitrocellulose membrane. Each of the covered gels was then covered with 2 sheets of filter paper and transferred into a transfer chamber. This chamber was filled with transfer buffer (25 mM Tris, pH 8.3, containing 192 mM glycine and 20% methanol) and the transfer of the polypeptides was performed at 4° C. during 12 hours and an amperage of 100 mA.

Thereafter, the nitrocellulose membranes were incubated first at room temperature for 4 hours in PBS [Maniatis et al., supra] containing 5% dried skimmed milk. Then, one of the nitrocellulose membranes was incubated at room temperature for 4 hours in PBS containing 5% dried skimmed milk and HIV-1-positive serum diluted 1:1000, and the other membrane was incubated at room temperature for 4 hours in PBS containing 5% dried skimmed milk and HIV-2 positive serum diluted 1:1000. Thereafter, the nitrocellulose membranes were washed first 3x with PBS containing 0.3% Tween-20 and thereafter incubated at room temperature for 1 hour in PBS containing 0.3% Tween 20.5% goat serum and goat-anti-human-IgG-peroxidase conjugate diluted 1:2000. After three washings with PBS, the protein bands on the nitrocellulose membranes which had reacted with antibodies were visualized by incubation in 25 ml of PBS containing 5 μg of 4-chloro-1-naphthol and 5 μl of 30% hydrogen peroxide. The reaction was stopped by the addition of PBS.

As shown in FIG. 10, the ENV(60)-DHFR and DHFR-ENV(60) polypeptides were recognized only by antibodies in the serum of patients infected with HIV-2. The ENV(80)-DHFR polypeptide was recognized only by antibodies in the serum of patients infected with HIV-1.

Example 6

Construction of Plasmid pRBSII-6xHis
A. Description of Plasmid pDS56/RBSII

For the construction of plasmid pRBSII-6xHis, plasmid pDS56/RBSII was used. E. coli cells transformed with this plasmid and with the plasmid pDMI,1 were deposited under the Budapest Treaty at the Deutschen Sammlung von Mikroorganismen in Braunschweig on Dec. 23, 1987 [E. coli M15 (pDS56/BSII; pDMI,1), DSM No.: 4330].

The part of pDS56/RBSII (FIGS. 11 and 12) which lies between the cleavage sites for the restriction enzymes XbaI and XhoI and which contains the replication region and the gene for β-lactamase, which confers ampicillin resistance to the cells, was derived originally from plasmid pRB322 (Bolivar et al., supra: Sutcliffe, supra). However, the gene for β-lactamase was modified by eliminating the cleavage sites for the restriction enzymes HincII and PstI. These alterations in the DNA sequence did not, however, affect the amino acid sequence of the part of an EcoRI/BamHI fragment. The terminator $t_o$ of β-lactamase. The remaining part of the plasmid carries the regularable promoter/operator element N25OPSN25OP29 followed by the ribosomal binding site RBSII, which is part of an EcoRI/BamHI fragment. The terminator $t_0$ of the E. coli phage lambda (Schwarz et al., supra), the promoter-free gene of chloramphenicol acetyltransferase (Marcoli et al., supra) and the terminator T1 of the E. coli rrnB operon (Brosius et al., supra) follow.

Because of the high efficiency of the expression signals N25OPSN25OP29 and RBSII, plasmid pDS56/RBSII and derivatives thereof such as plasmid pRBSII-6xHis can only be stably maintained in E. coli cells when the promoter/operator element is repressed by the binding of a lac repressor to the operator (see Example 2. Section A).

B. Construction of Plasmid pRBSII-6xHis 2 pmol of plasmid pDS56/RBSII were cleaved with the restriction enzyme HindIII. After working up the sample, 50 pmol of a phosphorylated adaptor (which codes for 6 histidines) were added to the cleaved plasmid DNA, and the sample was incubated with T4-DNA ligase as described above. After working up the ligation mixture, the DNA was cleaved with the restriction enzymes BamHI and XbaI and the BamHI/XbaI, fragment containing the region coding for 6 histidines, the terminator $t_0$, the cat gene and the terminator T1 was isolated by agarose gel electrophoresis (FIG. 13).

2 pmol of plasmid pDS56/RBSII were cleaved with the restriction enzymes XbaI and BamHI, and the XbaI/BamHI fragment containing the replication region, the bla gene, the promoter N25OPSN25OP29 and the ribosomal binding site RBSII was isolated by agarose gel electrophoresis (FIG. 14).

0.1 pmol of each of the isolated fragments were ligated and subsequently transformed into E. coli strain M15 (pDMI,1) as described above (Example 2). After plating and incubation (Example 2.B) individual colonies were grown in 10 ml of medium, as described, and the plasmid DNAs were isolated according to the method of Birnboim and Doly (supra). A restriction analysis with the enzymes BamHI and XbaI indicated that the plasmids contained the 2 desired fragments. These plasmids were designated pRBSII-6xHis (FIG. 14).

Example 7

Construction of Plasmid pRBSII-env(80)-gag(419)-env(60)-6xHis

A) Principles

For the construction of plasmid pRBSII-env(80)-gag(419)-env(60)-6xHis, the HIV-2 gene env(60) and the HIV-1 genes env(80) and gag(419) were linked with the expression vector pRBSII-6xHis.

B) Preparation of Plasmid pRBSII-6xHis Cleaved with the Restriction Enzymes BamHI and BglII 2 pmol of plasmid pRBSII-6xHis were cleaved with 10 units of the restriction enzymes BamHI and BglII. After adding sample buffer, the DNA was separated in a 1% agarose gel. After staining with ethidium bromide, the band corresponding to the plasmid DNA was cut out under UV light (300 nm) and purified by electroelution (Maniatis et al., supra). The ends of the purified DNA were then dephosphorylated with phosphatase. Subsequently, the DNA was extracted with phenol: chloroform (1:1), precipitated with ethanol and dissolved in ¼ TE buffer.

C) Preparation of the HIV-1 Gag(419) Gene 2 pmol of plasmid pU-GAG, which contains a SstI/BglII fragment of the HIV-1 gag gene (the nucleotide sequence of which is shown in FIG. 16), were digested with 12 units of the restriction enzyme XmnI. Subsequently, the DNA was extracted with phenol: chloroform (1:1) and precipitated with 2 volumes of ethanol at −20° C. The DNA pellet was resuspended in 50 μl of 50 mM Tris-HCl, pH 7.6, containing 10 mM MgCl$_2$, 10 mM DTT, 0.5 mM ATP, 100 pmol phosphorylated 10 mer BamHI-linker (5'-CCGGATCCGG-3'). After adding one unit of T4-DNA ligase, the mixture was incubated at 14° C. overnight. The mixture was then incubated at 65° C. for 10 minutes and brought to a volume of 100 μl with restriction enzyme buffer. 100 units of BamHI and 10 units of HindIII were added, and the mixture was incubated at 370° C. for 3 hours. Subsequently, the DNA was extracted with phenol and chloroform and precipitated with ethanol. The DNA pellet was dissolved in sample buffer and separated in a 6% polyacrylamide gel. After staining with ethidium bromide a band having 250 base pairs was cut out and isolated by electroelution.

2 pmol of the plasmid p2-3U/HindIII10, which contains a HindIII fragment of the HIV-1 gag gene (the sequence of which is shown in FIG. 17), were digested at 37° C. for one hour with 11 units of BglII, heated to 65° C. for 10 minutes, cooled to room temperature and incubated for 45 minutes with the Klenow fragment of E. coli DNA polymerase. Thereafter, the DNA was extracted with phenol: chloroform (1:1), precipitated with ethanol, taken up in 50 μl of 50 mM Tris-HCl, pH 7.6, containing 10 mM MgCl$_2$, 10 mM DTT, 0.5 mM ATP, 100 pmol phosphorylated 12 met BglII-linker (5'-GGAAGATCTTCC-3') and 1 unit of T4-DNA ligase and incubated at 14° C. overnight. The reaction mixture was then heated to 65° C. and brought to a volume of 100 μl with restriction enzyme buffer. 100 units of BglII were added and thereafter the mixture was incubated at 37° C. for 3 hours. After adding NaCl (50 mM final concentration) 10 units of HindIII were added and the mixture was incubated at 37° C. for 1 hour. After extraction with phenol: chloroform (1:1) the DNA was precipitated with ethanol and subsequently separated in a 1% agarose gel. A fragment having 1020 base pairs was cut out and isolated and purified by electroelution.

1 pmol each of the BamHI-HindIII fragment and the HindIII-BglII fragment were linked with each other using 1 unit of T4-DNA ligase. After heat inactivation of the ligase the ligated fragments were cleaved with BamHI and BglII and separated in a 1% agarose gel. The fragment corresponding to the HIV-1 gag(419) gene was isolated and purified by electroelution (FIG. 15).

D) Preparation of the HIV-1 Env(80) Gene

The preparation of the HIV-1 env(80) gene was carried out as described by Certa et al. [EMBO J.5, 3051–3056 (1986)].

E) Preparation of the HIV-2 Env(60) gene

The preparation of the HIV-2 env(60) gene is described in Example 1.

F) Construction of Plasmid pRBSII-gag(419)-6xHis

For the construction of plasmid pRBSII-gag(419)-6xHis, 0.1 pmol of the vector pRBSII-6xHis (see B) linearized with BamHI and BglII was linked with 0.3 pmol of the gag(419) gene by incubation with 1 unit of T4-DNA ligase at 14° C. overnight. After heat inactivation of the enzyme, the DNA was transformed into E. coli strain W3110 containing plasmid pDMI,1. The cells were plated onto LB agar plates containing 100 μg/ml ampicillin and 25 μg/ml kanamycin. The plates were incubated at 37° overnight. Individual colonies were grown at 37° C. overnight, and their plasmid DNAs were isolated using standard methods [Maniatis et al., supra](FIG. 18).

G) Construction of Plasmid pRBSII-env(80)-gag(419)-6xHis

For the construction of plasmid pRBSII-env(80)-gag (419)-6xHis, 0.1 pmol of plasmid pRBSII-gag(419)- 6xHis were cleaved with BamHI and treated with CIP. The DNA was extracted with phenol: chloroform (1:1) and precipitated with 2 volumes of ethanol. The pRBSII-gag(419)-6xHis plasmid DNA linearized with BamHI was incubated at 14° C. overnight with 0.3 pmol of the HIV-1 env(80) gene and 1 unit of T4-DNA ligase. After heat inactivation of the enzyme, the DNA was transformed into E. coli strain W3110, which contained the plasmid pDMI,1. The cells were plated onto LB agar plates containing 100 μg/ml ampicillin and 25 μg/ml kanamycin. The plates were incubated at 37° C. overnight. Individual colonies were grown at 37° C. overnight, and their plasmid DNAs were isolated using standard methods [Maniatis et al., supra](FIG. 19).

H) Construction of Plasmid pRBSII-env(80)-gag(419)-env (60)-6xHis

For the construction of plasmid pRBSII-env(80)-gag (419)-env(60)-6xHis, 0.1 pmol of plasmid pRBSII-env (80) -gag(419)-6xHis was cleaved with BglII and treated with CIP. Subsequently, the DNA was extracted with phenol: chloroform (1:1) and precipitated with 2 volumes of ethanol. Plasmid pRBSII-env(80)-gag(419)-6xHis DNA linearized with BglII was then incubated at 14° C. overnight with 0.3 pmol of the HIV-2 env(60) gene and 1 unit of T4-DNA ligase. After heat inactivation of the enzyme, the DNA was transformed into E. coli strain W3110 containing the plasmid pDMI,1. The cells were plated onto LB agar plates containing 100 μg/ml ampicillin and 25 μg/ml. kanamycin. The plates were incubated at 37° C. overnight. Individual colonies were grown at 37° C. overnight and their plasmid DNAs were isolated using standard methods [Maniatis et al., supra] (FIG. 20).

Example 8

Reactivity of the ENV(80)-GAG(419)-ENV(60) Polypeptide with HIV-Positive Sera

A. Principles

To demonstrate that the ENV(80)-GAG(419)- -ENV(60) polypeptide reacts with sera of persons infected with HIV-1 and HIV-2, the ENV(80)-GAG(419)-ENV(60) polypeptide was expressed in E. coli, purified and tested with suitable sera in an enzyme immunoassay (EIA).

B. Expression of the ENV(SO)-GAG(419.)-ENV(60) Polypeptide in E. coli

E. coli W3110 cells containing plasmid pDMI,1 were transformed with plasmid pRBSII-env(80)-gag(419)-env (60)-6xHis and grown in LB medium [Maniatis et al., supra] containing 100 μg/ml ampicillin and 25 μg/ml kanamycin. The culture was induced with IPTG (2 mM final conc.) at an optical density of OD$_{600}$=1.0 and grown for 2 hours. Thereafter, the cells were harvested by centrifugation.

C. Purification of the ENV(80)-GAG(419)-ENV(60) Polypeptide Expressed in E. coli The harvested cells were re-suspended in PBS buffer (0.2 g/l KCl, 8.0 g/l NaCl, 0.2 g/l KH$_2$PO$_4$, 1.144 g/l Na$_2$HPO$_4$, pH 7.0) and disrupted using a high pressure homogenizer. The cell homogenizate obtained was centrifuged, and the pellet was extracted twice, with 0.1M sodium phosphate buffer, pH 8.0, containing 6M guanidine.HCl.

Undissolved material was removed by centrifugation and, where required, filtered. The clarified solution was applied to a NTA column (the structure and production of which are described in European Patent Application Publication No. 253 303). The column was washed with 0.1M sodium phosphate buffer, pH 8.0, containing 6M guanidine.HCl and then with 0.1M sodium phosphate buffer, pH 6.5, containing 8M urea. The elution of the ENV(80)-GAG(419)-ENV(60) polypeptide was carried out with 0.1M sodium phosphate buffer, pH 4.0, containing 8M urea.

The ENV(80)-GAG(419)-ENV(60) obtained using the NTA column was subsequently chromatographed twice in a Sephacryl® S-200 column [Pharmacia, elution buffer: 50 mM Tris.HCl, pH 7.0, containing 5 mM EDTA and 1% SDS (first pass) or 0.1% SDS (second pass). By SDS polyacrylamide gel electrophoresis and amino acid analysis, the purified ENV(80)-GAG(419)-ENV(60) polypeptide was shown to be 89% pure.

D. Reactivity of the Purified ENV(80)-GAG(419)-ENV(60) Polypeptide with HIV-positive Sera The purified ENV(80)-GAG(419)-ENV(60) polypeptide was tested for its reactivity with HIV-1 and HIV-2 positive sera in an enzyme immunoassay (EIA) as described in European Patent Application Publication No. 270 114. The EIA values obtained with purified ENV(80)-GAG(419)-ENV(60) polypeptide and purified DHFR-ENV(60) polypeptide (positive HIV-2 control) gave the following results:

| Sera | DHFR-ENV(60) HIV-2 | ENV(80)-GAG(419)-ENV(60) HIV-1/HIV-2 |
|---|---|---|
| HIV-1 positive sera[1] | | |
| Mil 3 | 0.132 | 1.684 |
| Mil 22 | 0.104 | 2.094 |
| Mil 24 | 0.140 | 2.244 |
| Mil 26 | 0.062 | 2.198 |
| Mil 30 | 0.059 | 2.345 |
| HIV-2 positive sera[1] | | |
| S | 1.271 | 2.072 |
| K | 0.910 | 2.052 |
| D | 1.559 | 2.252 |
| B | 1.232 | 2.104 |
| Negative sera | | |
| N1 | 0.096 | 0.092 |
| N2 | 0.047 | 1.110 |
| N3 | 0.063 | 0.076 |
| N4 | 0.056 | 0.087 |
| N5 | 0.067 | 0.088 |

[1] confirmed by "Western blots" (WB).

As can be seen, all positive HIV-1 and HIV-2 sera were recognized by the ENV(SO)-GAG(419)-ENV(60) polypeptide.

What is claimed is:

1. A polypeptide having the amino acid sequence

SerAlaArgLeuAsnSerTrpGlyCysAlaPheArgGlnValCysHisThrThr
ValProTrpValAsnAspSerLeuAlaProAspTrpAspAsnMetThrTrpGln
GluTrpGluLysGlnValArgTyrLeuGluAlaAsnIleSerLysSerLeuGlu
GlnAlaGlnGly.

2. A polypeptide having an amino acid sequence selected from the group consisting of:

MetArgGlySerHisHisHisHisHisHisGlySerAlaArgLeuAsnSerTrp
GlyCysAlaPheArgGlnValCysHisThrThrValProTrpValAsnAspSer
LeuAlaProAspTrpAspAsnMetThrTrpGlnGluTrpGluLysGlnValArg
TyrLeuGluAlaAsnIleSerLysSerLeuGluGlnAlaGlnGlySerGlyIle
MetValArgProLeuAsnCysIleValAlaValSerGlnAsnMetGlyIleGly
LysAsnGlyAspLeuProTrpProProLeuArgAsnGluPheLysTyrPheGln
ArgMetThrThrThrSerSerValGluGlyLysGlnAsnLeuValIleMetGly
ArgLysThrTrpPheSerIleProGluLysAsnArgProLeuLysAspArgIle
AsnIleValLeuSerArgGluLeuLysGluProProArgGlyAlaHisPheLeu
AlaLysSerLeuAspAspAlaLeuArgLeuIleGluGlnProGluLeuAlaSer
LysValAspMetValTrpIleValGlyGlySerSerValTyrGlnGluAlaMet
AsnGlnProGlyHisLeuArgLeuPheValThrArgIleMetGlnGluPheGlu
SerAspThrPhePheProGluIleAspLeuGlyLysTyrLysLeuLeuProGlu
TyrProGlyValLeuSerGluValGlnGluGluLysGlyIleLysTyrLysPhe
GluValTyrGluLysLysGlySerArgSerValAsnLeuVal, and MetArgGlySerHisHisHisHisHisHisGlySerGlyIleMetValArgPro
LeuAsnCysIleValAlaValSerGlnAsnMetGlyIleGlyLysAsnGlyAsp
LeuProTrpProProLeuArgAsnGluPheLysTyrPheGlnArgMetThrThr
ThrSerSerValGluGlyLysGlnAsnLeuValIleMetGlyArgLysThrTrp
PheSerIleProGluLysAsnArgProLeuLysAspArgIleAsnIleValLeu
SerArgGluLeuLysGluProProArgGlyAlaHisPheLeuAlaLysSerLeu
AspAspAlaLeuArgLeuIleGluGlnProGluLeuAlaSerLysValAspMet
ValTrpIleValGlyGlySerSerValTyrGlnGluAlaMetAsnGlnProGly
HisLeuArgLeuPheValThrArgIleMetGlnGluPheGluSerAspThrPhe
PheProGluIleAspLeuGlyLysTyrLysLeuLeuProGluTyrProGlyVal
LeuSerGluValGlnGluGluLysGlyIleLysTyrLysPheGluValTyrGlu
LysLysGlySerArgSerAlaArgLeuAsnSerTrpGlyCysAlaPheArgGln
ValCysHisThrThrValProTrpValAsnAspSerLeuAlaProAspTrpAsp
AsnMetThrTrpGlnGluTrpGluLysGlnValArgTyrLeuGluAlaAsnIle
SerLysSerLeuGluGlnAlaGlnGlySerValAsnLeuVal.

3. The polypeptide of claim 1 having an additional methionine residue at the amino terminus.

4. A polypeptide having the formula:

A-B-C,

A-C-B, or

C-B-A wherein

A is an affinity peptide

B is

SerAlaArgLeuAsnSerTrpGlyCysAlaPheArgGlnValCysHisThrThr
ValProTrpValAsnAspSerLeuAlaProAspTrpAspAsnMetThrTrpGln
GluTrpGluLysGlnValArgTyrLeuGluAlaAsnIleSerLysSerLeuGlu
GlnAlaGlnGly, and C is a carrier polypeptide.

5. The polypeptide of claim 4 having an additional methionine residue at the amino terminus.

* * * * *